(12) United States Patent
Payne et al.

(10) Patent No.: US 6,723,082 B1
(45) Date of Patent: Apr. 20, 2004

(54) DELIVERY CATHETER SYSTEM FOR HEART CHAMBER

(76) Inventors: Sam G. Payne, 2175 Hoover Dr., Santa Clara, CA (US) 95051; Randy J. Kesten, 181 Ada Ave. #41, Mountain View, CA (US) 94043; Michael Aita, 4067 N. Farwell Ave., Shorewood, WI (US) 53211; Stewart M. Kume, 2309 Buena Vista Ave., Belmont, CA (US) 94002; Stephen B. Pearce, 2250 Monroe St. #273, Santa Clara, CA (US) 95051; Manuel A. Javier, Jr., 768 Valley Way, Santa Clara, CA (US) 95050

(*) Notice: Subject to any disclaimer, the term of this patent is extended or adjusted under 35 U.S.C. 154(b) by 0 days.

(21) Appl. No.: 09/405,937

(22) Filed: Sep. 27, 1999

Related U.S. Application Data

(63) Continuation-in-part of application No. 09/052,971, filed on Mar. 31, 1998, which is a continuation-in-part of application No. 09/053,146, filed on Mar. 31, 1998, now abandoned, which is a continuation-in-part of application No. 08/962,530, filed on Oct. 31, 1997, which is a continuation-in-part of application No. 08/646,856, filed on May 8, 1996, now abandoned, which is a continuation-in-part of application No. 08/438,743, filed on May 10, 1995, now abandoned.

(51) Int. Cl.$^7$ ............................................. A61M 25/01
(52) U.S. Cl. ..................................................... 604/528
(58) Field of Search ................................ 604/22, 95.04, 604/95.03, 95.01, 95.02, 523, 525, 528, 530; 606/21, 41; 600/136, 139, 146, 149, 143, 150

(56) References Cited

U.S. PATENT DOCUMENTS 4,784,638 A * 11/1988 Ghajar et al. ................. 604/49
5,147,334 A * 9/1992 Moss ........................... 604/264
6,086,582 A * 7/2000 Altman et al. ................. 606/41
6,176,856 B1 * 1/2001 Jandak et al. .................. 606/29
6,179,809 B1 * 1/2001 Khairkhahan et al. ... 604/95.04
6,210,362 B1 * 4/2001 Ponzi ....................... 604/95.01
6,224,566 B1 * 5/2001 Loeb ............................ 604/22
6,251,418 B1 * 6/2001 Ahern et al. ................. 424/423

FOREIGN PATENT DOCUMENTS

WO     WO 96/35469     11/1996     .......... A61M/25/00

* cited by examiner

Primary Examiner—Manuel Mendez
(74) Attorney, Agent, or Firm—Gibson, Dunn & Crutcher LLP

(57) ABSTRACT

Apparatus and methods for delivering an angiogenic agent to a site within the heart. Either using a percutaneous, intraoperative or minimally invasive approach, an elongated member containing an angiogenic agent is guided to a heart wall and the agent is dispensed into heart tissue. Additional fluids or substances can be dispensed in combination with the angiogenic agent to provide visualization and site mapping. In certain embodiments, the angiogenic agent is delivered adjunctively with the administration of energy, such as laser energy or RF energy which disturbs the heart tissue sufficiently to enhance the effects of the angiogenic agent. A delivery catheter system for delivering a substance delivery member into a patient's left ventricle which includes a first delivery catheter with a shaped distal extremity configured to be aligned with or parallel to a longitudinal axis or long dimension of the patient's left ventricle and a second delivery catheter slidably and rotatably disposed within an inner lumen of the first delivery catheter which has a shaped distal shaft section and an inner lumen configured to slidably receive a substance delivery member such as an elongated cannula slidably disposed within a polymer sheath.

9 Claims, 15 Drawing Sheets

DELIVERY CATHETER SYSTEM FOR HEART CHAMBER

RELATED APPLICATIONS

This application is a continuation-in-part of copending application Ser. No. 09/052,971, filed on Mar. 31, 1998, entitled DELIVERY CATHETER SYSTEM FOR HEART CHAMBER, which is a continuation-in-part of copending application Ser. No. 08/962,530, filed Oct. 31, 1997, entitled GUIDING CATHETER SYSTEM FOR ABLATING HEART TISSUE, which is a continuation-in-part of application Ser. No. 08/646,856, filed on May 8, 1996, now abandoned entitled SYSTEM AND METHOD FOR TREATING OR DIAGNOSING HEART TISSUE, which is a continuation-in-part of application Ser. No. 08/438,743, filed on May 10, 1995, now abandoned entitled DELIVERY SYSTEM AND METHOD FOR MYOCARDIAL REVASCULARIZATION, all of which are incorporated herein in their entirety by reference. This application is also a continuation-in-part of application Ser. No. 09/053,146, filed on Mar. 31, 1998, now abandoned entitled DELIVERY OF AN ANGIOGENIC SUBSTANCE, which is incorporated by reference in its entirety.

BACKGROUND OF THE INVENTION

This invention relates to the diagnosis and/or treatment of a patient's heart and particularly to the delivery of therapeutic or diagnostic devices and agents to a patient's heart tissue from within the patient's heart chamber.

Coronary artery disease affects the lives of millions of patients worldwide. Many therapies are available for atherosclerosis, including CABG surgery to bypass blocked arteries, PTCA interventions to attempt to restore patency, stents that also attempt to maintain patency, atherectomy to remove the collected plaque, and a number of pharmacological approaches that attempt to reduce the effects of narrowing of vessel lumens, by the stenosis, by reducing the amount of plaque or by altering the hemodynamic characteristics of the patient's blood. While the aforesaid procedures provide well known clinical improvements, none provide a fully satisfactory long term therapy. The presently available pharmacological therapies are of limited value. Ideally, a non-invasive pharmacological or genetic therapy would facilitate reperfusion of the ischemic myocardium, either by restoring patency, or by creating new blood vessels to supply the ischemic region with additional oxygenated blood.

A number of different substances and techniques are known for attempting to treat coronary artery disease by the administration of a therapeutic substance to a patient. One common method of administration is systemic administration. For example, EPO Application EP 314105 discloses the oral administration or intramuscular injection of an "angiogenesis enhancer." U.S. Pat. No. 5,480,975 discloses treating hypoxic tissue damage by local or topical administration of a transition metal compound to induce VEGF expression, either by local administration or topical application. The indirect nature of these routes of administration are generally less desirable and not universally applicable to all forms of substances that might be used to treat ischemic myocardium.

Using a catheterization procedure to deliver a substance to the vessels in the vicinity of the stenosis is also known. For example, PCT Application WO 9723256 discloses the percutaneous delivery of an angiogenic factor to a vessel wall through the lumen of a catheter. The distal end of the catheter is provided with infusion ports that engage the vessel wall when the catheter is expanded, and infusion may be enhanced by providing needles or other penetrating elements. U.S. Pat. No. 5,681,278 discloses treating vascular thrombosis and angioplasty restenosis by administering a bioactive agent to an extravascular treatment site, particularly introducing such an agent proximally adjacent to the exterior of a coronary artery. U.S. Pat. No. 5,698,531 discloses site specific installation of cells or the transformation of cells by delivering proteins by catheterization to discrete blood vessel segments wherein the agent is situated on the walls of the blood vessel or perfused in the tissue of the vessel. U.S. Pat. No. 5,523,092 discloses an indwelling catheter for localized delivery of a substance into a tissue conduit without disrupting the fluid flow. U.S. Pat. No. 5,244,460 discloses the intracoronary arterial delivery of a blood vessel growth promoting peptide periodically over several days. None of these references, however, address the provision of a substance directly into the myocardial tissue.

Recent advances in biotechnology have shown great promise for treating coronary artery disease. In *Circulation* 1998, 97:645–650, Schumacher et al. report treating coronary heart diseases using human growth factor FGF-I (basic fibroblast growth factor) to induce neoangiogenesis in ischemic myocardium. The FGF-I was administered during a CABG procedure by injection into the myocardium distal to the IMA/LAD anastamosis and close to the LAD. The results reported demonstrate the efficacy of FGF-I treatment. However, administration by direct injection during surgery is less than optimal because it is as invasive to the patient as a CABG procedure. In addition, at least one fibroblast growth factor has also been delivered using a microparticle carrier delivered to an artery via a catheter in a non-ischemic model, as reported in *Nature Biotechnology* 1998; 16:134 and 159–160. The intra-arterial delivery of microparticles produced positive results, but was chosen so that the surrounding tissue would be undamaged. The article indicates that non-invasive techniques to deliver genes into peripheral ischemic myocardium tissue are presently unavailable.

Targeted delivery of therapeutic or diagnostic devices and/or agents is a desirable but often difficult task. For therapeutic and diagnostic devices the advantages include shorter and less traumatic procedures and for therapeutic and diagnostic agents the benefits include more efficient use of the agent and the limitation of the agent action to a desired region. Whether the delivery of a therapeutic or diagnostic device to a desired region of a patient's heart tissue from within the heart chamber thereof is successful and efficient is frequently the result of the physician's skill which can vary considerably from physician to physician and from day to day with the same physician. Accurate delivery of various substances to the tissue of a patient's heart wall can be a function of the same physician skill. Additionally, successful and effective substance delivery can also be a function of minimizing systemic loss, keeping the substance within the desired region, timing and ensuring a sufficient quantity of substance in the desired area for sufficient period of time to achieve the desired therapeutic or diagnostic effect.

U.S. Pat. No. 5,840,049, filed on Jun. 7, 1995, entitled THERAPEUTIC AND DIAGNOSTIC AGENT DELIVERY, describes a method and system for delivering a therapeutic or diagnostic agent by first forming a channel in a heart wall from within a heart chamber defined by the wall and then delivering or depositing the agent within the channel. Reference is made to the use of a laser to form the channel, particularly in conjunction with a transmyocardial revascularization procedure. U.S. Pat. No. 5,840,049 is hereby incorporated herein by reference in its entirety. Agents described in U.S. Pat. No. 5,840,049 include vascular endothelial growth factor (VEGF), acidic and basic fibroblast growth factors (aFGF, bFGF), angiogenin, nitric oxide, prostaglandin, prostaglandin synthase and other prostaglandin synthetic enzymes and isoforms of superoxide dismutase and other antioxidant proteins.

Coronary artery disease is also successfully treated by transmyocardial revascularization (TMR) alone, using methods and apparatus such as those disclosed in U.S. Pat. Nos. 5,380316, 5,389,096 and 5,54,152, all of which are incorporated herein by reference. Using intraoperative, minimally invasive or percutaneous techniques, energy is delivered directly to the myocardium in the ischemic area and as a result, a focal injury occurs. This focal injury is typically in the form of a small "channel" formed by a laser. It is believed that the focal injury acts to stimulate subsequent neovasculogenesis. Moreover, in addition to the reperfusion of the ischemic region, there is evidence that the disruption of certain afferent nerves in the tissue and other effects provides acute and chronic reduction in angina pain.

Suitable means for creating a site for angiogenesis were referenced in copending application Ser. No. 08/976,831, filed on Nov. 24, 1997 (Aita et al.), which is incorporated herein in its entirety. The application describes an intravascular system for myocardial revascularization which is introduced percutaneously into a peripheral artery and advanced through the patient's arterial system into the left ventricle of the patient's heart. The procedure affects only the endocardium and the myocardium from within the left ventricle. This procedure eliminates the need of the prior intraoperative procedures to open the chest cavity and to penetrate through the entire heart wall in order to form the channel through the endocardium into the myocardium.

While the percutaneous method and system for introducing therapeutic and diagnostic agents into a patient's heart wall as described in U.S. Pat. No. 5,840,049 represented a substantial advance, one of the difficulties with the procedure was that it was difficult to ensure delivery of all of the agent into the channel and keeping the agent within the channel for a sufficient period until the desired therapeutic or diagnostic affect occurred.

Thus, there exists a long felt, yet unmet need for methods and apparatus that permit the localized introduction of a substance into the myocardium directly, either during an intraoperative procedure or percutaneously. It would also be desireable to have an improved apparatus and improved techniques that will permit the adjunctive delivery of substances into localized areas within the myocardium efficaciously, efficiently and in a manner that can enjoy widespread adoption by cardiac surgeons and interventional cardiologists. What has also been needed is an improved delivery system and method for delivering a therapeutic or diagnostic device or agent into heart tissue from within the patient's heart chamber, particularly to provide access to all or substantially all of the endocardial surface from within the heart chamber for delivery of such agents and devices.

SUMMARY OF THE INVENTION

The present invention is directed to a system for delivering an elongated therapeutic or diagnostic device or agent into the wall of a patient's heart from within a chamber defined by the heart wall. The system of the invention has the capability to access tissue in the endocardial, myocardial, and epicardial layers of the heart wall, in addition to other areas of the heart. The invention provides access to a wide region of the patient's endocardial lining and the tissue beneath it. The system also accurately places and effectively holds the distal end of the system at one or more desired locations within the patient's heart chamber at a desired orientation, e.g. perpendicular or near perpendicular, with respect to the patient's endocardium. The perpendicular or near perpendicular orientation of the distal extremity of the cannula or other device with respect to the endocardial surface of the heart chamber is most desirable. As used herein the terms "normal" and "perpendicular" shall include variations of up to 30° from a normal or perpendicular orientation.

The delivery catheter system of the invention generally includes a first guiding or delivery catheter which has a relatively straight main shaft section and a shaped distal shaft section which is configured to have a discharge axis selected so that it is generally aligned with or parallel to the longitudinal axis of the patient's left ventricle. The discharge axis is herein defined to be the longitudinal axis of the most distal segment of the catheter described. The system also generally includes a second guiding or delivery catheter slidably and rotatably disposed within an inner lumen of the first delivery catheter and provided with a shaped distal section configured to have a discharge axis with a desired orientation.

The system of the invention also has substance delivery member for delivery of a therapeutic or diagnostic agent which is disposed within the inner lumen of the second delivery catheter. The substance delivery member is configured so it can be advanced into the wall of the patient's heart. The member preferably has an injector, which may be a syringe or other suitable device, provided on the proximal end of a cannula to deliver the diagnostic or therapeutic agent in a carrier fluid or gel or in solid form through the inner lumen of the cannula into the tissue of the patient heart wall.

Preferably, the distal extremity of the substance delivery member which extends out the distal end of the second delivery catheter has sufficient rigidity to penetrate the tissue of the heart, and be self-supporting within the environment of the heart chamber. Generally, the distal portion of the substance delivery member is considered as being "self supporting" if a force of at least 4 grams, preferably at least 8 grams, is required to deflect the free end of a cantilevered specimen 0.5 inch (12.7 mm) in length (span length) of cannula a distance of one millimeter. A sheath surrounding the cannula can also act to provide support.

In one preferred embodiment, an injector or syringe member containing a therapeutic or diagnostic agent is incorporated into the distal extremity of an elongated cannula slidably disposed within the inner lumen of the second delivery catheter for delivery of the agent into the heart wall. The agent may be in a carrier fluid or gel, or may be in a solid form. The injector is actuated at the proximal end of the delivery system which extends out of the patient. The injector may be set up for a single or multiple doses.

The location of the distal end of the substance delivery member within the heart chamber, and particularly with respect to the endocardial surface, can be detected fluoroscopically by providing a radiopaque marker on the distal extremity of the delivery member, either or both of the polymer sheath or elongated cannula, and optionally, either or both of the delivery catheters. The radiopaque marker can be made from a suitable metal, such as gold, platinum or tantalum, or the like, or a material such as $BaSO_4$ or Bismuth can be added to the material that forms the polymer sheath, or the first or second delivery catheter. The use of dye injections through a port in the distal end of first or the second delivery catheter may be employed to further facilitate the location of the distal end of these catheters. Other means such as a variety of proximity detectors, including ultrasonic proximity detectors, may be employed to detect contact between the distal end of the substance delivery member or the delivery catheters and the endocardium.

In accordance with one presently preferred embodiment of the present invention, the first delivery catheter has proximal and distal ends, a port in the distal end and an inner lumen extending within the catheter to the port in the distal end. The first delivery catheter has a relatively straight main shaft section and a preshaped distal section configured to point in a direction so that the discharge axis of this catheter is aligned with or parallel or near parallel to the longitudinal axis of the left ventricle or other chamber into which it is inserted. For many applications the first delivery catheter is about 90 to about 130 cm, preferably about 100 to about 120 cm in length.

The first delivery catheter preferably has a main shaft section and a shaped distal section with a first segment and a second segment which provide a discharge axis approximating the longitudinal axis or long dimension of the heart chamber. The first segment of the distal shaft section of the first delivery catheter should be at an angle of about 95° to about 160°, preferably about 100° to about 150° with respect to a proximally adjacent second segment of the distal shaft section. The proximally adjacent second segment should be at an angle of about 95° to about 160°, preferably about 100° to about 150° with respect to either the proximally adjacent main shaft section or a third segment of the distal shaft section proximally adjacent to the second segment. If there is a third segment of the distal section, it is at an angle of about 110° to about 170°, preferably about 120° to about 150° with respect to proximally adjacent main shaft section. The first and second segments should each be about 0.5 to about 5 cm, preferably about 0.5 to about 4 cm in length, with the total length of the shaped distal section with two segments being about 2 to about 6 cm. If the distal section has a third segment, it should have a length of about 1 to about 5 cm, preferably about 2 to about 4 cm. The length of the shaped distal section with three segments should be about 3 to about 8 cm, preferably about 4 to about 7 cm.

In another embodiment, the shaped distal section of the first delivery catheter has a single angled segment which provides a discharge axis approximating the longitudinal axis or long dimension of the heart or other chamber into which it is disposed. In this embodiment the single angled segment of the distal shaft section has a length of about 2 to about 8 cm, preferably about 4 to about 6 cm and is at an angle of about 95° to about 160°, preferably about 100° to about 140° with respect to a proximally adjacent portion of the main shaft section.

The second delivery catheter of the invention is longer than the first delivery catheter, and is slidably and preferably rotatably disposed within inner lumen of the first delivery catheter. The second delivery catheter likewise has proximal and distal ends, a port in the distal end and an inner lumen extending within the second delivery catheter to the port in the distal end. The second delivery catheter has a relatively straight main shaft section and a distal section which is at an angle of about 80° to about 140°, preferably about 90° to about 120° with respect to the main shaft section thereof. The second delivery catheter should be at least 10 cm longer, preferably about 15 to about 50 cm longer, than the first delivery catheter and is about 100 to about 150 cm, preferably about 110 to about 140 cm in length. The shaped distal section of the second delivery catheter should have a radius of curvature of about 2 to 30 mm, preferably about 4 to about 20 mm between the main shaft section and the exit or discharge axis through the port in the distal end of the shaped distal section. The length of the shaped distal section of the second delivery catheter is about 0.5 to about 4 cm, preferably about 1 to about 3 cm. The angles of the various segments of the distal section of the first and second delivery catheters facilitate directing the operative distal end of an elongated substance delivery member, which is slidably disposed within the inner lumen of the second delivery catheter, toward the region of the endocardium where the procedure is to be performed at an orientation that is preferably perpendicular or near perpendicular with the endocardial surface of the patient's heart wall.

The second delivery catheter is rotatably and slidably disposed within the inner lumen of the first delivery catheter to facilitate the desired placement and orientation of the shaped distal section of the second delivery catheter within the left ventricle, e.g. substantially normal to the endocardium. In this manner an elongated cannula slidably disposed within the inner lumen of the second delivery catheter or the injector at the distal extremity of the second delivery catheter is properly oriented with respect to the endocardial surface of the heart chamber in order to effectively be inserted into the heart wall. The elongated cannula may also be disposed within a polymer sheath which is slidably disposed with in the inner lumen of the second delivery catheter. The polymer sheath has a proximal end and a distal end, preferably with at least one penetration limiter disposed on the distal end of the polymer sheath. The sheath protects the tip from inadvertently damaging tissue or other parts of the catheter delivery system.

The distal sections of the first and second delivery catheters are preferably preformed into a desired shape so that they will provide a desired orientation for the delivery system when they extend into the patient's heart chamber. However, the catheters may alternatively be provided with control lines, pull wires, or other suitable means (e.g., a shape memory or a superelastic or pseudoelastic NiTi element) to deflect or otherwise shape the distal sections of the catheters once the distal extremity of the delivery system extends into the heart chamber. The system of the present invention essentially provides access at a desired normal or near normal orientation to the entire semi-conical inner surface of the free wall defining part the patient's heart chamber and the intraventricular septum.

The first and second delivery catheters are preferably relatively stiff catheters so that the position of the cannula or other substance delivery member will be maintained during the procedure even though the heart is beating and blood is flowing within the chamber. The delivery catheters, and particularly the first delivery catheter, are preferably provided with relatively stiff proximal and shaped distal sections with a more flexible intermediate section which is configured to be disposed within the patient's aortic arch during the procedure as described in copending application Ser. No. 08/813,503 entitled CATHETER WITH FLEXIBLE INTERMEDIATE SECTION and filed on Mar. 7, 1997, which is incorporated herein by reference.

In a presently preferred embodiment of practicing the method of the invention, the first delivery catheter of the delivery catheter system is introduced into a peripheral artery, such as the femoral artery, and advanced through the patient's arterial system until the distal end of the first catheter is disposed within the patient's left ventricle. The position of the first delivery catheter is adjusted by the physician under fluoroscopic observation or other techniques until its distal tip is oriented generally along or parallel to the longitudinal axis of the left ventricle. The second delivery catheter is advanced through the previously introduced first delivery catheter which has a distal end appropriately positioned within the left ventricle. The distal end of the second delivery catheter is then adjusted under flouroscopic visualization, or the like, until it is oriented perpendicular to the wall of the heart adjacent the tissue to be treated. The substance delivery member is then advanced distally until contact is made with the tissue of the heart wall. The elongated cannula is then advanced into the tissue to be treated, and the diagnositic or therapeutic substance injected with a syringe through the elongated cannula and out its distal end into the tissue to be treated.

The system of the invention has the capability to access tissue in the endocardial, myocardial, and epicardial layers of the heart wall, in addition to other areas of the heart. The invention provides access to a wide region of the patient's endocardial lining and the tissue beneath it which defines the heart chamber. The system also accurately places and effectively holds the distal end of the system at one or more desired locations within the patient's heart chamber at a desired orientation, e.g. perpendicular or near perpendicular, with respect to the patient's endocardium.

In another embodiment, an elongated device has a handpiece for delivering a metered dose of a substance via a delivery lumen. The elongated device may be either a catheter or an intraoperative probe, and in certain preferred embodiments has a reservoir containing the substance in a deliverable state, such as an angiogenic agent. Preferably, the device comprises a metered dispensing apparatus for injecting one or more appropriate doses and includes a dispensing control system, such as a switch disposed on the handpiece or a separate foot pedal. In some embodiments, the dispensing control system is automated, and preferably, a signal generated by the heart is provided to a circuit synchronizing the activation of the automated dispensing apparatus to the cardiac cycle. For example, the apparatus may be synchronized to the patient's ECG by a circuit which inhibits activating the dispensing apparatus during a predetermined portion of the cardiac cycle.

In some embodiments, the delivery device has a distal end which is configured for penetration into the patient's tissue, e.g., has a sharp or needle-like distal end, and has at least one orifice in fluid communication with a lumen extending through the distal extremity of the device which is in fluid communication with the one or more orifices and a source of therapeutic or diagnostic substance. Additionally, in certain embodiments, the distal end has one or more radially oriented lumens to direct the substance to be delivered laterally within the patient's tissue. Another aspect of certain embodiments of the present invention relates to contacting the tissue to be treated with the distal end. For example, elongated elements such as bristles or barbs may be provided that deploy from a first position inhibiting tissue contact to a second position permitting tissue contact are provided in some embodiments. Preferably, the elongated elements are aligned with a longitudinal axis of the device and disposed along an outside surface so they deploy from a first position that inhibits tissue engagement to a second position that permits tissue engagement. In other embodiments, the distal end can have an enlarged or bulbous section, which may or may not be expandable.

Other aspects of certain embodiments of the present invention include providing the device with a radiopaque marker disposed at the distal end to aid in the fluoroscopic visualization thereof during the procedure and providing a depth stop to limit device penetration depth. One preferred embodiment of a depth stop is the construction of a section of the distal end smaller in diameter than a second section immediately proximal of the distal section and a shoulder connecting the distal section and the second section that acts as the depth stop. Alternatively, the depth stop can be one or more mechanical elements or arms that extend out radially from the distal end. In other embodiment, visualization of the dose is accomplished by the administration of a marker substance either along with or in addition to the therapeutic substance such as an angiogenic agent. In another aspect of the present invention, multiple lumen catheters or probes are provided with one of the plurality of lumens being used to deliver the substance such as an angiogenic agent, while other lumens may be utilized to deliver other fluids, substances, or apparatus.

In certain embodiments, the present invention may also be provided with a distal tissue contact device for energy delivery to the myocardium to perform a procedure that dissects, disturbs, disrupts or ablates the tissue region to which the substance is injected. The distal tissue contact device may be one of a number of known apparatus whereby energy is delivered to the myocardium to perform a procedure that dissects, disturbs, disrupts or ablates the tissue. For example, the distal tissue contact device can be a mechanical device affixed to the distal end, or it can be a device such as a laser energy conductor, an RF energy conductor, an ultrasound transducer, or a current conductor. In another preferred embodiment, the distal tissue contact device can be a lumen in a device connected to a source of fluid at a pressure and velocity sufficient to disrupt tissue. In any of these embodiments, the distal tissue contact device is preferably introduced using a lumen separate from a lumen carrying the therapeutic or diagnostic substance to be delivered.

Thus, one preferred embodiment of the present invention broadly discloses an injector apparatus synchronized to a cardiac cycle signal that has a conduit with a least one lumen connected on a proximal end to an injection device and, preferably, a solenoid connected to the injection device. In use, a controlled amount of a substance to be delivered is dispensed when the solenoid is pulsed by a signal related to the cardiac cycle. Preferably, the solenoid advances the same amount after each of one or more pulses, so that more than one injection can be given in each heartbeat if desired. When an embodiment including a distal tissue contact device is used, an activation switch is also provided and energy is introduced into the heart tissue by operation of the activation switch, preferably but not necessarily in synchronization with the cardiac cycle.

Another additional aspect of the present invention is the provision of an apparatus for delivering a bolus of substance that has a delivery lumen extending from a distal end to a proximal point distal to the proximal end, and wherein at least a first section of the delivery lumen is filled with the substance to be delivered. In certain embodiments a second section of the delivery lumen in fluid communication with the first section is provided that contains a second substance other than the first which may aid in delivery or visualization of the first substance when it is delivered. In any embodiment, it is preferred, though not required, that the substance, i.e., an angiogenic agent, is in a fluidic or thixotropic state to facilitate delivery. In one presently preferred embodiment, the delivery lumen contains at least an angiogenic agent and a marker substance.

Although it will be readily understood that the percutaneous and intraoperative versions of the present invention may differ markedly in construction, each device may have one or more of a number of features addressed below. The discussion of these features of a substance delivery system is thus not specific to or limited to either the percutaneous or intraoperative embodiments.

As used herein, the term "angiogenic agent" includes any material or substance useful in a procedure that promotes the growth of new vessels, particularly the growth of new vessels in the myocardium, however, it will be understood that an angiogenic effect is useful in other organs, such as the liver and kidneys. The methods and apparatus of the present invention may employ a wide variety of angiogenic agents, including small molecule drugs, active compounds and cellular and gene therapy agents. Examples of active compounds include, by way of non-limiting example, biologically active carbohydrates, recombinant biopharmaceuticals, agents that are active in the regulation of vascular physiology, such as nitric oxide agents that effect the regulation of gene activity by modulating transcription, the turnover of cellular mRNA, or the efficiency with which specific mRNA is translated into its protein product, i.e., antisense pharmaceuticals. Other active compounds include hormones, soluble receptors, receptor ligands, peptides (both synthetic and naturally occurring), peptidomimetic compounds, specific and non-specific protease inhibitors, postaglandins, inhibitors of prostaglandin synthase and/or other enzymes involved in the regulation of prostaglandin synthesis, growth factors that affect the vascualture such as the fibroblast growth factors (FGF's), acidic (aFGF, FGF-II) and basic fibroblast growth factors (bFGF, FGF-I), vascular endothelial growth factors (VEGF), angiogenin, transforming growth factor alpha, and transforming growth factor beta. The foregoing list is meant to illustrate the breadth of angiogenic agents and other substances useful with the present invention and is not meant to be exhaustive or in any way limit the scope of the invention. It is contemplated that there are classes of angiogenic agents possessing structures significantly similar to other molecular agents, and that these agents will have specific biological activities associated with them while being deficient in other biological activities that are less desirable therapeutically. Any and all of the angiogenic agents useful with the present invention may comprise substantially pure compounds, defined or relatively less well defined admixtures of compounds, such as those that might result from a biological system such as conditioned serum or conditioned cell culture media.

Finally, any reference to "angiogenic agent" herein will be understood to include diagnostic agents and markers useful with the present invention. Such diagnostic agents or markers may be delivered before, after or during the administration of the angiogenic agent itself, and include any substances used to ascertain the physical location, configuration or physiologic state of a tissue or tissues, e.g., dyes, stains, diagnostic challenge agents and agents such as radiopaque agents used to enhance contrast during diagnostic or therapeutic procedures such as myogenic compounds, anesthetic agents or chemical sypathectomy agents.

These and other advantages of the invention will become more apparent from the following detailed description of the invention, when taken in conjunction with the accompanying exemplary drawings.

DETAILED DESCRIPTION OF THE INVENTION

Figure 1:
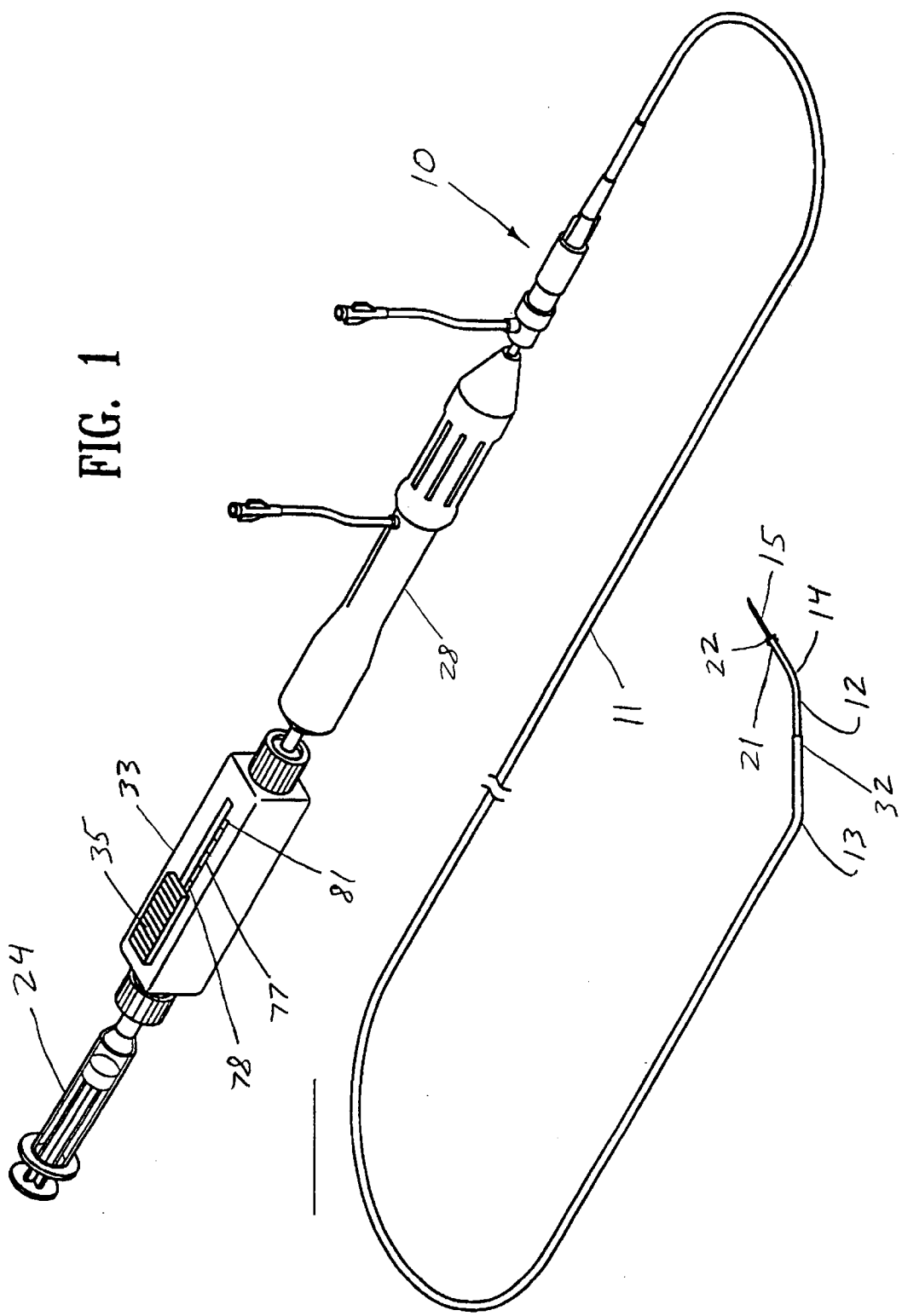
FIG. 1 is a perspective view of an embodiment of the present invention.

FIG. 1 illustrates an embodiment of the invention which is a delivery catheter system 10 having a first delivery catheter 11 and a second delivery catheter 12 which is longer than the first delivery catheter and slidably and rotatably disposed within the first delivery catheter. Preferably the first delivery catheter 11 has an angled distal shaft section 13 and the second delivery catheter 12 has an angled distal shaft section 14. The angled distal shaft sections 13 and 14 of the delivery catheters 11 and 12 can be proximally manipulated and positioned relative to each other by translation and rotation to achieve a desired position and angular orientation during a procedure.

Referring to FIGS. 1 and 2, and FIGS. 9–11, a substance delivery member 15, which is preferably an elongated cannula 16 slidably disposed within a polymer sheath 17, is slidably disposed within the second delivery catheter 12 such that a distal end 18 of the polymer sheath can extend beyond a distal end 21 of the second delivery catheter 12 and engage the desired tissue of a heart wall. Preferably, at least one penetration limiter 22 is operatively disposed on the distal end of the polymer sheath 18. A proximal end 23 of the elongated cannula 16 is in fluid communication with an injector 24 which forces a therapeutic or diagnostic substance 25 from the injector into the proximal end of the elongated cannula, out the distal end 26 of the elongated cannula, and into tissue to be treated.

Figure 2:
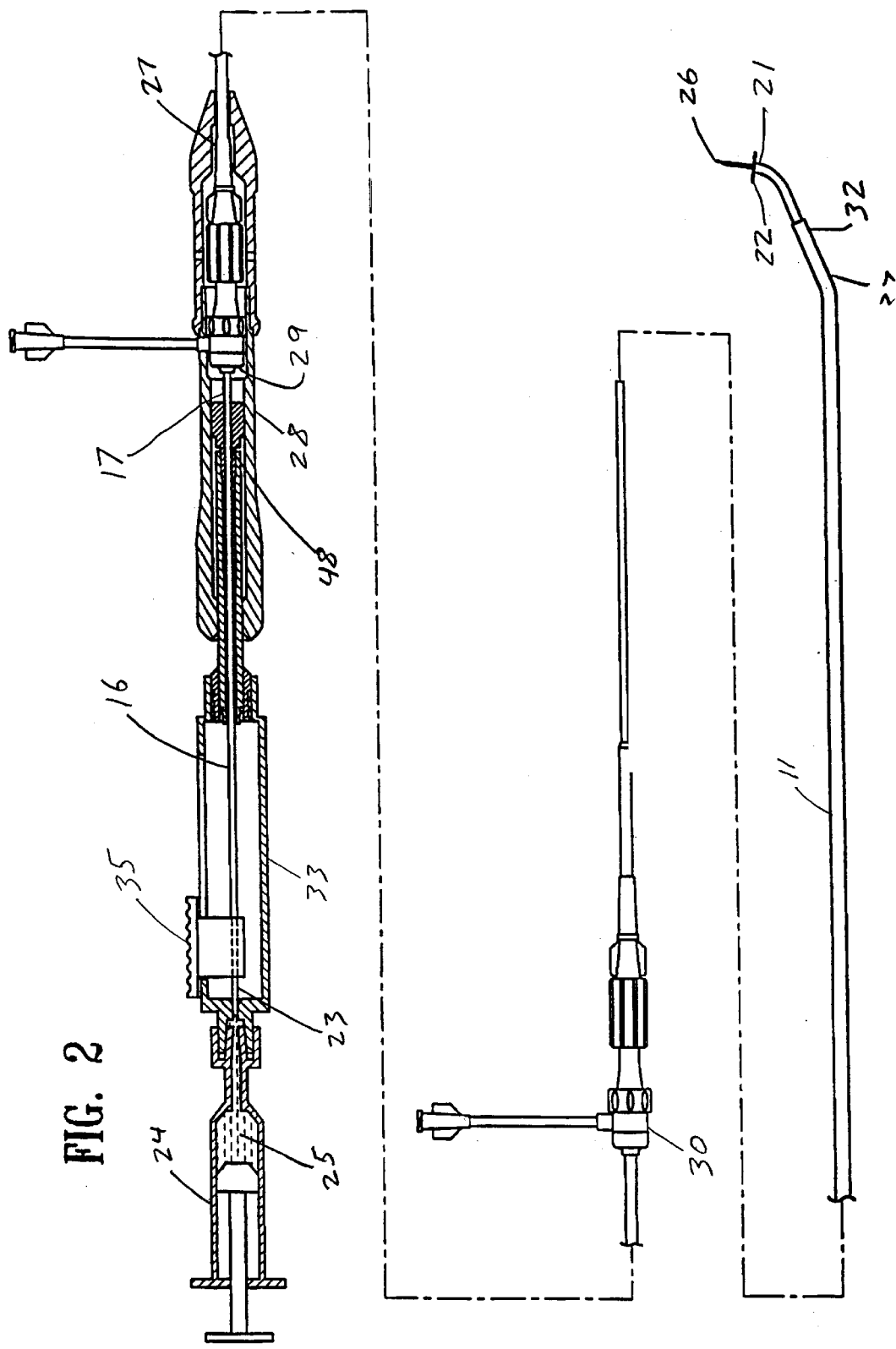
FIG. 2 is an elevational view of the proximal assembly.

Referring to preferred embodiments of the invention illustrated in FIG. 1 and FIG. 2, the proximal end 27 of the second delivery catheter 12 is fixed within the proximal controller 28 by a proximal hemostasis member 29 which is disposed within the proximal controller, and mechanically engages and seals the proximal end 27 of the second delivery catheter and the polymer sheath 17. Thus, fluids that are forced into the distal end 21 of the second delivery catheter under pressure, such as blood, can not leak out the proximal end 27 of the second delivery catheter at the point where the polymer sheath exits said proximal end of the second delivery catheter. However, axial movement between the polymer sheath 17 and the second delivery catheter 12 is still provided for, notwithstanding the seal therebetween. The first delivery catheter 11 is sealingly engaged to the proximal end 27 of the second delivery catheter by a distal hemostasis member 30.

Because the second delivery catheter 12 is fixed to the proximal controller 28 by the proximal hemostasis member 29, movement of the proximal controller 28 relative to the first delivery catheter 11 moves the first delivery catheter in relation to the second delivery catheter. By such relative movement, the angle that the distal end 21 of the second delivery catheter makes with the distal end 32 of the first delivery catheter can be adjusted. This is possible because the distal end 21 of the second delivery catheter will conform to some degree or a large degree, depending on the relative stiffness of the two delivery catheters 11 and 12, to the shape and direction of the distal end 32 of the first delivery catheter 11.

The illustrated embodiment of the invention also has an advancement controller 33 which is located proximally and slidably coupled to the proximal controller 28. The polymer sheath 17 is attached at the distal end 34 of the advancement controller 33 and the elongated cannula is attached to a slider 35 which remains stationary with respect to the advancement controller 33, unless deliberately moved relative thereto. Therefore, movement of the advancement controller 33 in relation to the proximal controller 28 moves the polymer sheath 17 and elongated cannula 16 in relation to the second delivery catheter 12. The slider 35 is mechanically attached to the proximal end 23 of the elongated cannula 16 and is slidably disposed upon the advancement controller 33.

Translating the slider 35 relative to the advancement controller 33 proportionally translates the elongated cannula 16 in relation to the polymer sheath 17 which surrounds at least a substantial portion of the elongated cannula. In this way, once the distal end 21 of the second delivery catheter 12 is properly positioned adjacent tissue to be treated by translation and rotation of the first delivery catheter 11 and second delivery catheter, the distal end of the polymer sheath 18 can be advanced distally to contact the tissue by movement of the advancement controller relative to the proximal controller. The distal end of the elongated cannula 26, which preferably includes a sharp 36, can then be extended into the tissue by distally advancing the slider 35 relative to the advancement controller 33, and a desired therapeutic substance injected into the tissue by the injector 24.

Figure 3:
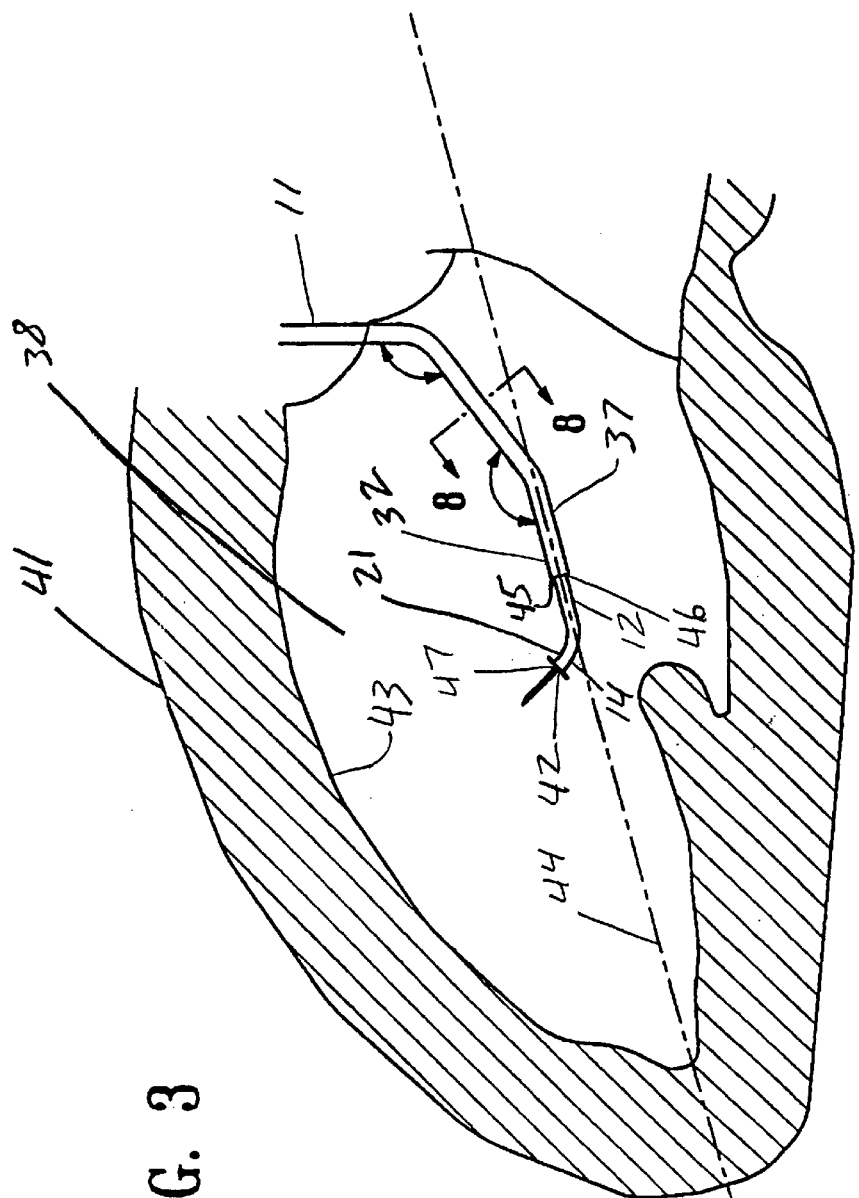
FIG. 3 is an elevational view of a delivery catheter system embodying features of the invention with the distal extremity of the system disposed within the patient's left ventricle, which is seen in a left lateral cutaway view.

FIG. 3 schematically illustrates a distal end 37 of one presently preferred embodiment of the delivery catheter system 10 of the invention disposed within the left ventricle 38 of a patient's heart 41. Once the distal end 21 of the second delivery catheter 12 is properly positioned adjacent tissue surface 43 in the heart 41 by translation and rotation of the first delivery catheter 11 and second delivery catheter, the distal end of the polymer sheath 18 can be advanced to contact the tissue surface by movement of the advancement controller 33 relative to the proximal controller 28. The distal end of the elongated cannula 26 can then be extended into the tissue by distally advancing the slider 35 relative to the advancement controller 33, and a therapeutic or diagnostic substance injected into the tissue by the injector 24.

In a presently preferred method of the invention, the first delivery catheter 11 is first introduced into the patient's arterial system preferably by means of the Seldinger technique through the femoral artery and advanced through the patient's arterial system including the aorta until a distal end 32 of the first delivery catheter 11 is disposed at a desired location within the left ventricle 38 generally aligned with or parallel to the longitudinal axis 44 of the left ventricle 38. The second delivery catheter 12 and the polymer sheath 17 which at least partially surrounds the elongated cannula 16, or some other suitable substance delivery member, may then be advanced together or sequentially through the inner lumen 45 of the first delivery catheter 11 into the left ventricle 38. The second delivery catheter 12 is advanced out of, rotated within or withdrawn into the inner lumen 45 of the first delivery catheter to orient the distal end 21 of the second delivery catheter 12 toward a desired region within the left ventricle 38 where the procedure is to be performed.

The distal shaft section 14 of the second delivery catheter 12 is preshaped so that it forms the desired shape when exiting the port 46 in the distal end of the first delivery catheter 32. The distal end 18 of the polymer sheath may then be advanced through the inner lumen of a second delivery catheter 42 and out a port 47 in the distal end 21 thereof until contact is achieved with the tissue surface 43. Preferably pressure is applied to the polymer sheath 17 from its proximal end 48 so as to maintain contact with the tissue of the heart 41 when deploying the sharp 36 of the elongated cannula 16. The axial force applied to the proximal end 48 of the polymer sheath 17 via the advancement controller 33 is preferably sufficient to ensure contact with tissue of the heart wall 41, but the force should not exceed the level which will cause a distal tip 18 of the polymer sheath 17 surrounding the elongated cannula 16 to mechanically penetrate heart tissue 41. Preferably, penetration of the distal end 18 of the polymer sheath is prevented at least in part by at least in part penetration limiter 22 disposed on the distal end of the polymer sheath. The penetration limiters 22 are preferably composed of shape memory or psuedoelastic alloy, such as Nitinol, however any suitable material having the appropriate mechanical characteristics can be used.

Once contact is made with the tissue of the area to be treated, the elongated cannula 16 having a sharp 36 may be advanced into the tissue to the desired depth by advancing the slider 35 which is slidably housed in the advancement controller 33 and which is mechanically coupled to the proximal end 23 of the elongated cannula 16. Once the distal tip 51 of the elongated cannula 16 is in position, the therapeutic or diagnostic substance 25 is delivered out of the distal tip 51 by activating the injector 24 which forces the substance into the proximal end 23 of the elongated cannula and out of the distal tip 51 into the tissue to be treated. The elongated cannula 16 may then be withdrawn and the procedure repeated in another location until the desired amount of substance 25 has been delivered. An alternative method would incorporate an embodiment of the invention whereby the injector 24 and substance to be delivered 25 are disposed upon the distal end 37 of the delivery catheter system 10 and the therapeutic or diagnostic substance 25 is injected directly into the tissue by remote activation of the injector.

Generally, the overall length of the polymer sheath 17 and the elongated cannula 16 are longer than the second delivery catheter 12 and are preferably configured to extend out of the second delivery catheter a distance of up to about 15 cm, preferably about 4 to about 10 cm to perform the desired therapeutic or diagnostic procedure. The polymer sheath 17 and elongated cannula 16 should have the flexibility required to pass through the inner lumen 42 of the second delivery catheter 12.

Figure 4:
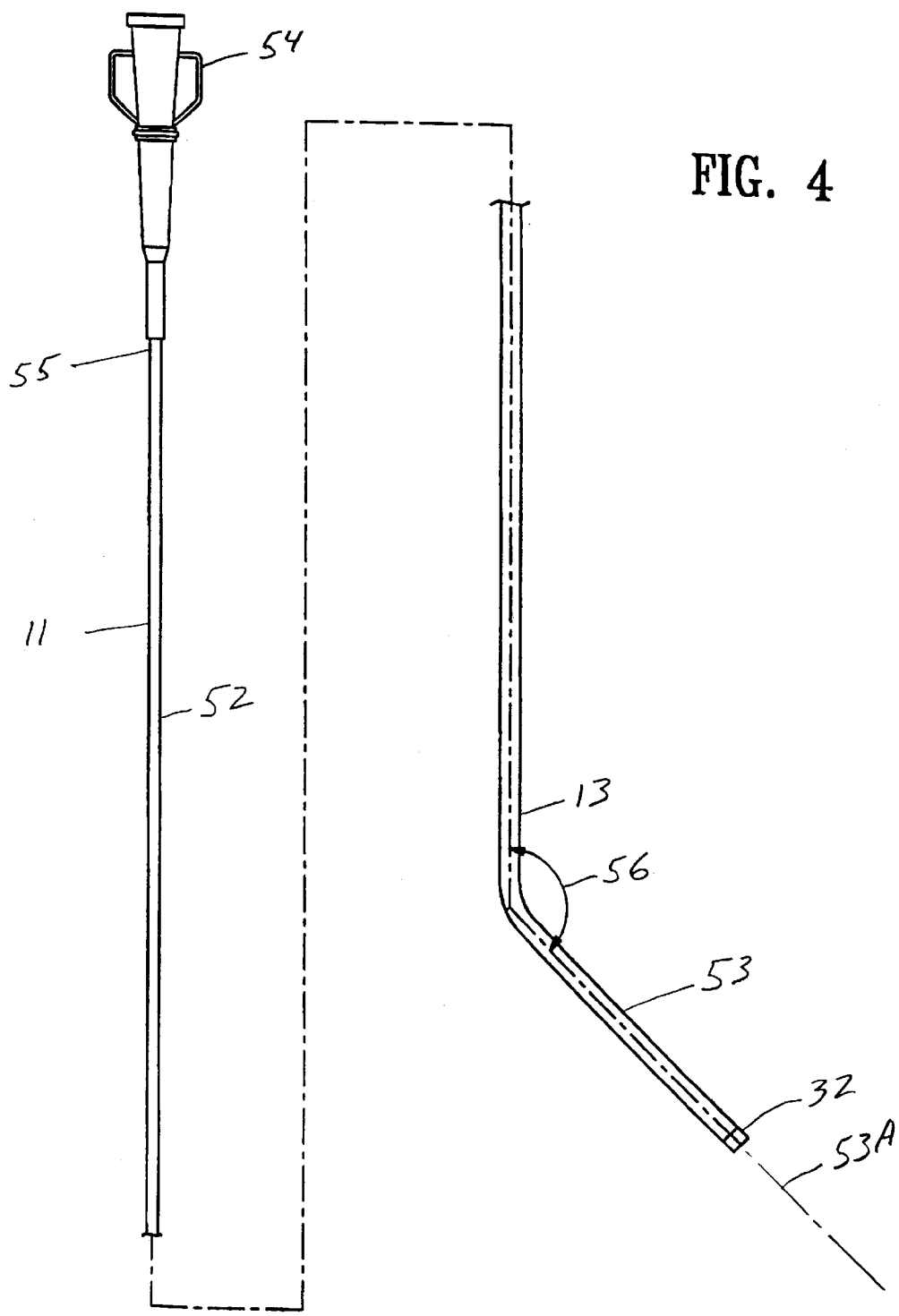
FIG. 4 is an elevational view of an alternative first delivery catheter having a shaped distal section with a single distal segment.

FIG. 4 illustrates an embodiment of the first delivery catheter 11 which has a main shaft section 52 and a shaped distal shaft section 13 with a first angled distal segment 53. The discharge axis 53A of the first delivery catheter 11 is shown extending from the first distal segment 53. The overall length of the first delivery catheter 11 is about 70 to about 130 cm, the outer diameter is about 0.1 to about 0.15 inch (2.5–3.75 mm) and the diameter of the inner lumen 45 about 0.07 to about 0.1 inch (1.8–2.5 mm). An adapter 54 is provided on a proximal end 55 of the main shaft section. In this embodiment the first angled segment 53 of the distal shaft section 13 has a length of about 1 to about 9 cm and forms an angle 56 of about 90 to about 150°, preferably about 105 to about 140°, with respect to the proximally located main shaft section 52.

Figure 5:
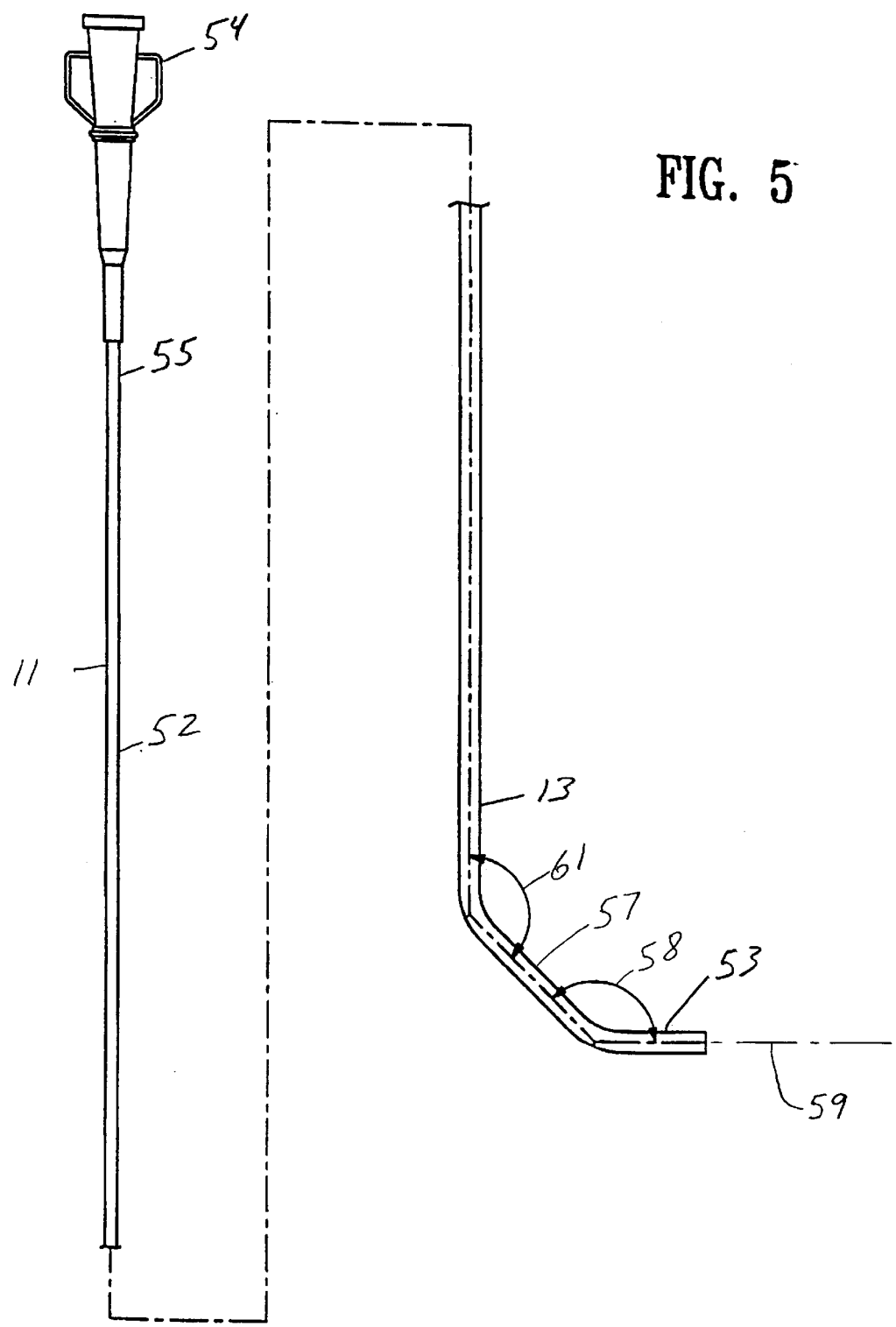
FIG. 5 is an elevational view of the first delivery catheter shown in FIG. 3.

The embodiment of the first delivery catheter 11, as shown in FIG. 5, has a shaped distal shaft section 13 with a first segment 53 and a second segment 57. The first segment 53 is shaped to be at an angle 58 with respect to the proximally adjacent second segment 57. The second segment 57 is shaped to be at an angle 61 with respect to the proximally adjacent main shaft section 52. The angle 58 the first segment 53 makes with respect to the proximally adjacent second segment 57 can be from about 90 to about 160°, preferably about 100 to about 150°. The discharge axis 59 of the first delivery catheter 11 is shown extending from the first segment 53. The angle 61 the second segment 57 makes with respect to the proximally adjacent main shaft section 52 can be from about 95 to about 165°, preferably about 100 to about 150°. The segments 53 and 57 of the distal shaft section 13 of the first delivery catheter 11 are angled to discharge the second delivery catheter 12 generally along or parallel with the longitudinal axis 44 of the left ventricle 38.

Figure 6:
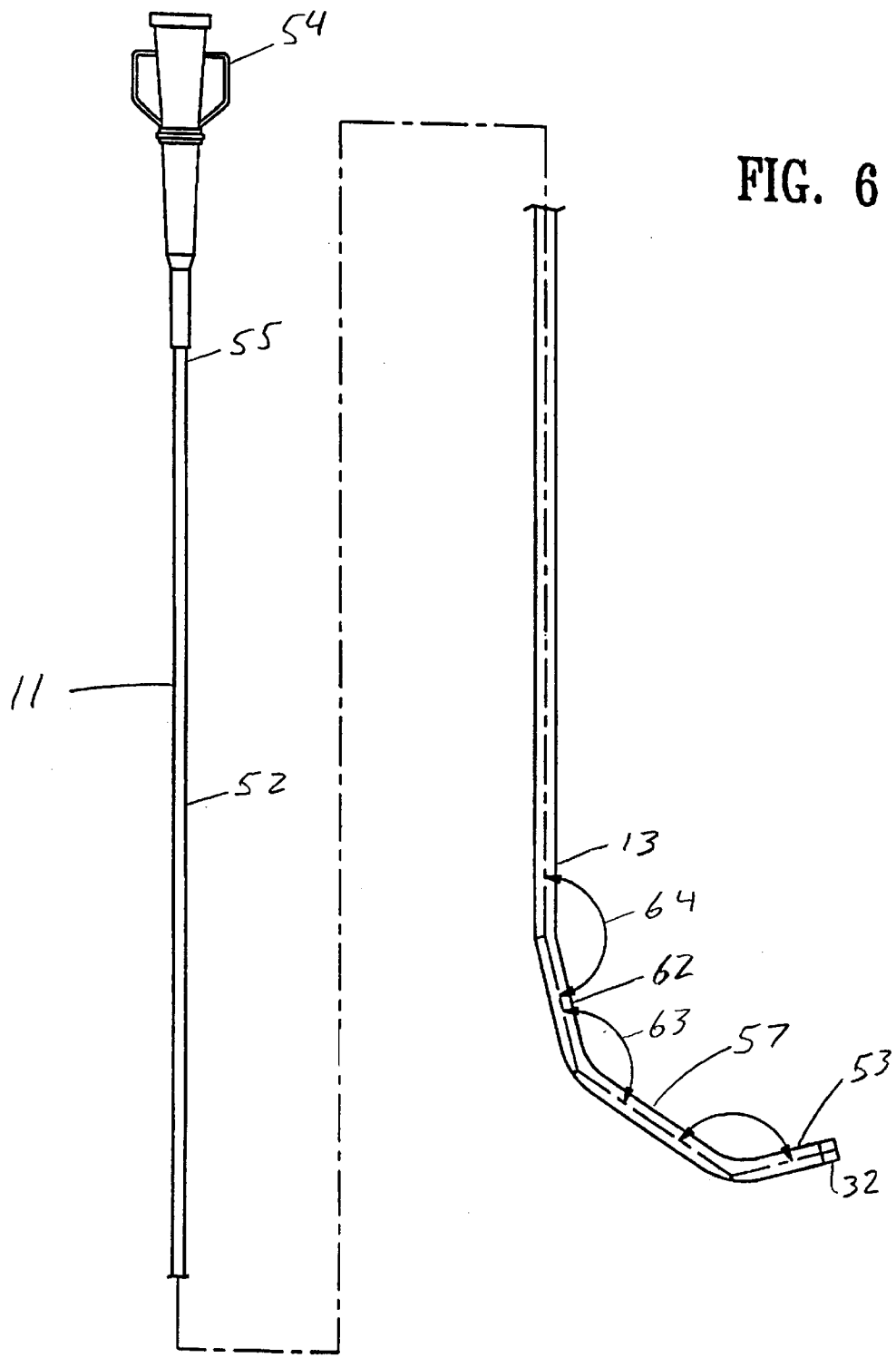
FIG. 6 is an elevational view of an alternative first delivery catheter having a shaped distal section with three segments.

Another alternative embodiment of the invention is shown in FIG. 6 where a first delivery catheter 11 is provided with a main shaft section 52 and a shaped distal shaft section 13 comprising three distal segments, a first segment 53, a second segment 57 and a third segment 62. The first segment 53 is angled with respect to the second segment 57 similarly to the embodiment described above which has two distal section segments. The angle 63 the second segment 57 makes with respect to the third segment 62 can be from about 95 to about 160°, preferably about 100 to about 135°. The third segment 62 makes an angle 64 with respect to the proximally adjacent main shaft of about 110 to about 170°, preferably about 120 to about 150°. An adapter 54 is provided on the proximal end of the main shaft section 55.

Figure 7:
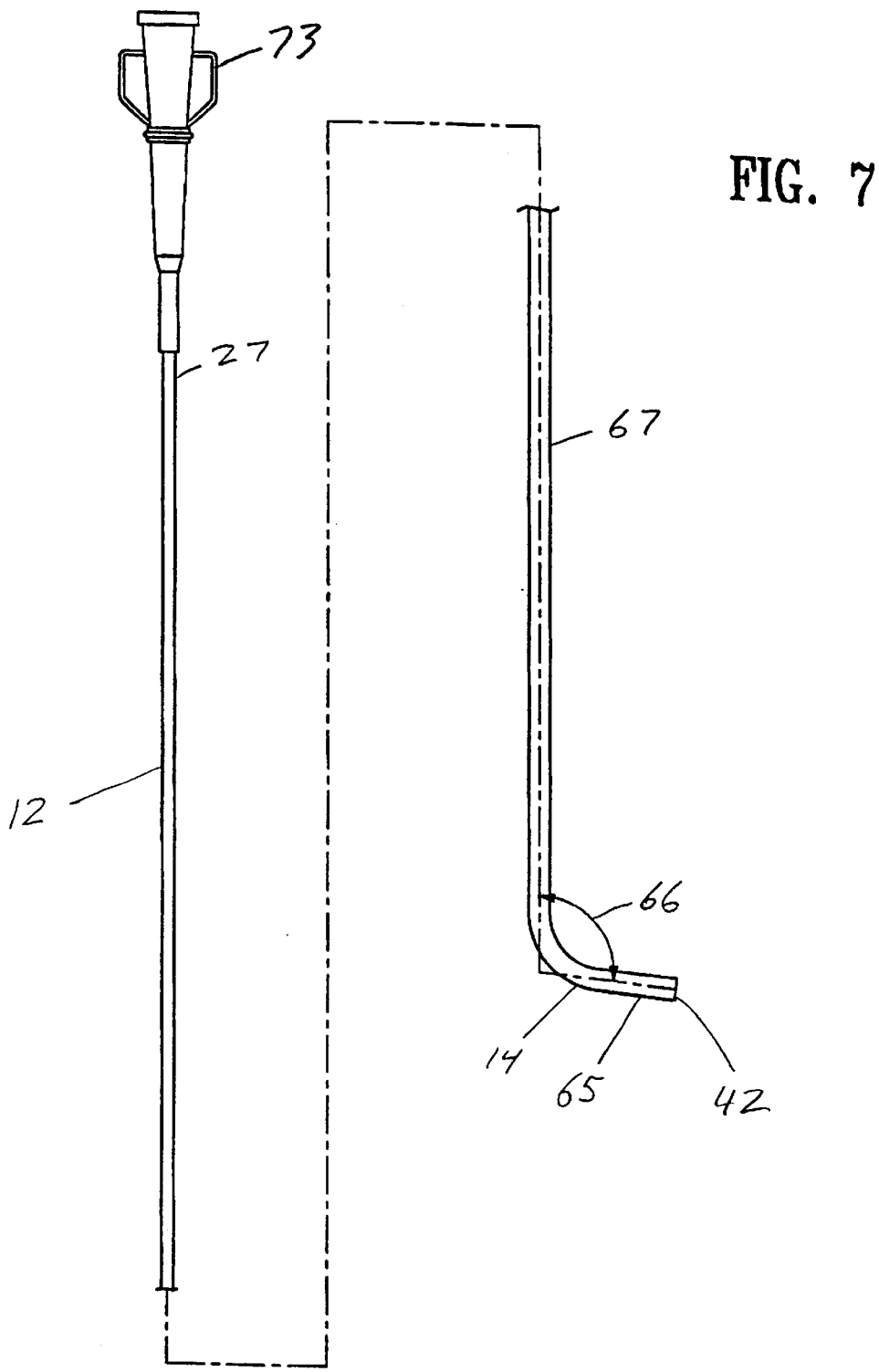
FIG. 7 is an elevational view of the second delivery catheter shown in FIG. 3.

The second delivery catheter 12, shown in FIG. 7, has a shaped distal shaft section 14 with a first segment 65 which is at an angle 66 with respect to a main shaft section 67 of the second delivery catheter 12 to ensure that the discharge axis thereof is perpendicular or near perpendicular with the region of the heart wall 41 in which the procedure is to be performed. The angle 66 of the first segment 65 of the distal shaft section of the second delivery catheter 12 with respect to the main shaft section 67 of the second delivery catheter can be from about 70 to about 150°, preferably about 90 to about 120°.

Figure 8:
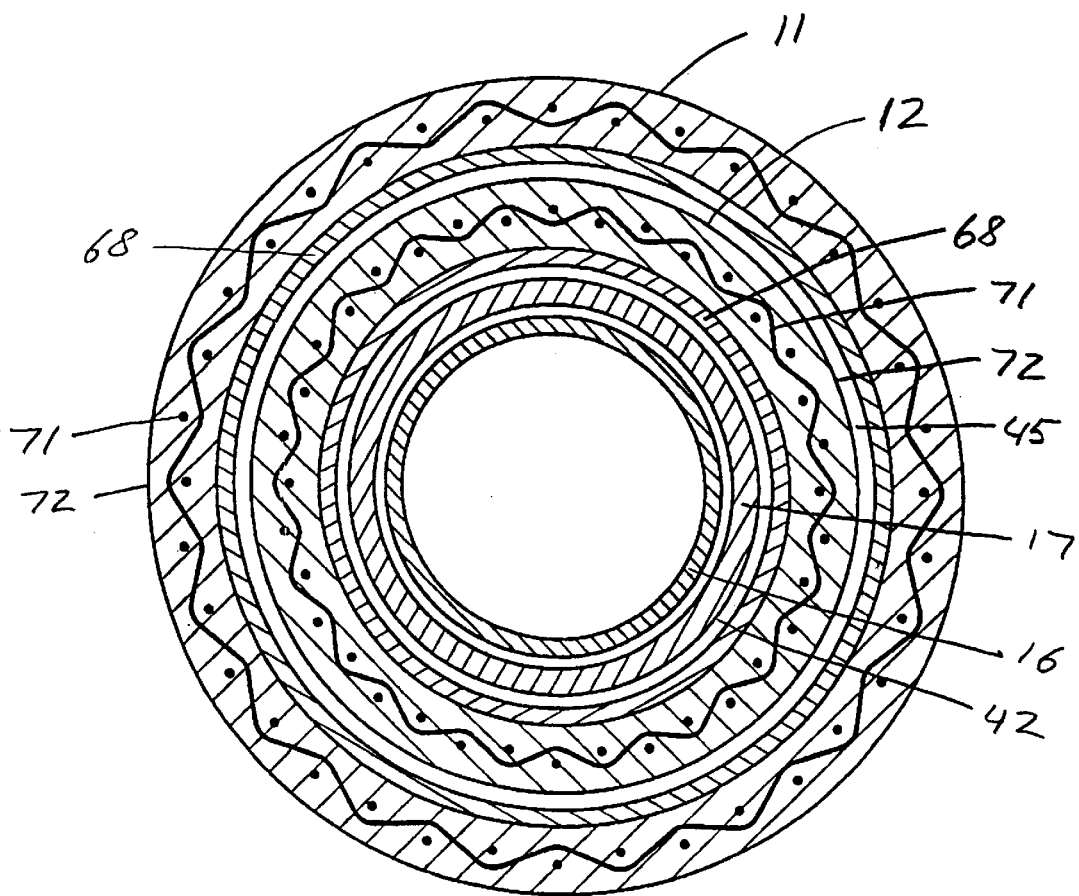
FIG. 8 is a transverse cross sectional view of the delivery catheter system shown in FIG. 3 taken along lines 8—8.

Referring to FIG. 8, the second delivery catheter 12 has a structure similar to or the same as the first delivery catheter 11 and has a lubricious lining 68, a fiber reinforcement 71 which may be braided or wound and an outer polymer jacket 72. The outer diameter of the second delivery catheter 12 is configured so that it can be readily moved longitudinally and readily rotated within the inner lumen 45 of the first delivery catheter 11 by manipulating the proximal end 27 of the second delivery catheter 12 which extends out of the patient. An adapter 73 is provided on the proximal end 27 of the second delivery catheter 12 for the introduction of therapeutic substances 25 and diagnostic devices.

The overall length of the second delivery catheter 12 is about 10 to about 40 cm longer than the first delivery catheter 11 to ensure that both the distal end 21 and the proximal end 27 of the second delivery catheter 12 can simultaneously extend out the distal end 32 and the proximal end 55 respectively of the first delivery catheter 11 so that movement of the distal end of the first delivery catheter can be effected by manipulation of the proximal end. The outer diameter of the second delivery catheter 12 is about 0.04 to less than about 0.1 inch (1–2.5 mm) and the diameter of the inner lumen 42 of the second delivery catheter is about 0.02 to about 0.07 inches (0.5–1.8 mm).

Referring again to FIG. 7, the junction between the first segment 65 and the main shaft section 67 of the second delivery catheter 12 should have a radius of curvature from about 2 to about 30 mm, preferably about 4 to about 20 mm to allow for the passage of a therapeutic or diagnostic device such as a substance delivery member 15. The radius of curvature need not be constant along the length of the curved section 14. For example, the curvature can increase progressively in the distal direction along the length of the distal shaft section 14 of the catheter.

As shown in greater detail in FIG. 8, the first delivery catheter 11 and second delivery catheter 12 may be of conventional guiding catheter construction, which can include a wall structure having a inner lubricious lining 68, a fiber reinforcement 71 in a polymer matrix which may be braided or wound and an outer jacket 72 which may be formed of suitable polymeric material in a conventional manner, e.g. extruding onto the fiber reinforcement. Suitable polymers include polyethylene, polyurethane and the like. The strands of the fiber reinforcement 71 may be stainless steel, or other suitable high strength materials including suitable polymeric materials such as Kevlar® or Nylon. The lubricious inner liner 68 may be formed of a suitable fluoropolymer such as poly(tetrafluoro)ethylene which is sold under the trademark Teflon®. The first delivery catheter 11 may be provided with a soft, nontraumatic distal tip 32 to facilitate advancement of the catheter through a patient's vasculature without significant damage to the vessel lining. The second delivery catheter 12 may be of similar construction to that described above regarding the first delivery catheter, although the second delivery catheter 12 need not have a non-traumatic tip.

Figure 9:
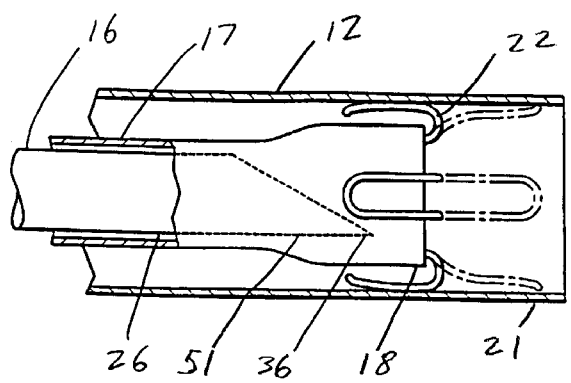
FIG. 9 is an elevational view in partial section of the distal end of the substance delivery member where the penetration limiters are in a constrained position.
Figure 10:
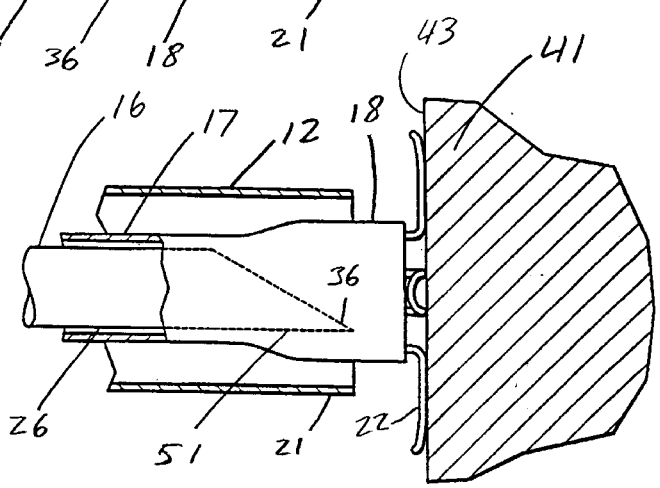
FIG. 10 is an elevational view in partial section of the distal end of the substance delivery member where the penetration limiters are in an expanded position.

In FIG. 9, it can be seen that when the distal end 21 of the second delivery catheter 12 is introduced into the vasculature, the distal end 18 of the polymer sheath 17 is preferably disposed proximally of the distal end 21 of the second delivery catheter, and the distal end 26 of the elongated cannula is in a similar position, thereby permitting a smooth introduction of the polymer sheath and elongated cannula into the second delivery catheter. The polymer sheath 17 and the second delivery catheter 12 may slide relative to one another, to either extend or retract, as necessary. The polymer sheath 17 is preferably made from a nylon or polyimide material, but may be made from any suitable polymer such as polytetraflouroethylene, sold under the trademark Teflon®, polyurethane, polypropylene, or the like. In FIG. 10, in which it is seen that the distal end 18 of the polymer sheath 17 extends beyond the distal end 21 of the second delivery catheter.

One aspect of preferred embodiments of the present invention is the provision of penetration limiters 22 on the distal end 18 of the polymer sheath 17. The provision of penetrating limiters 22 aids and enhances the use of the present invention by providing a safeguard and assurance to the user as to the position of the distal end 18 of the polymer sheath relative to the penetration of the elongated cannula 16. Additionally, the penetration limiters 22 can provide stability while the device is in place and the wall of the heart 41 continues to move. Although the present invention is useful without penetration limiters 22, it is believed that the provision of a penetration limiter or at least an enlarged diameter (not shown) at the distal end of the polymer sheath 18 will foreclose the possibility of the distal end of the polymer sheath 18 breaking the tissue surface 43.

Figure 11:
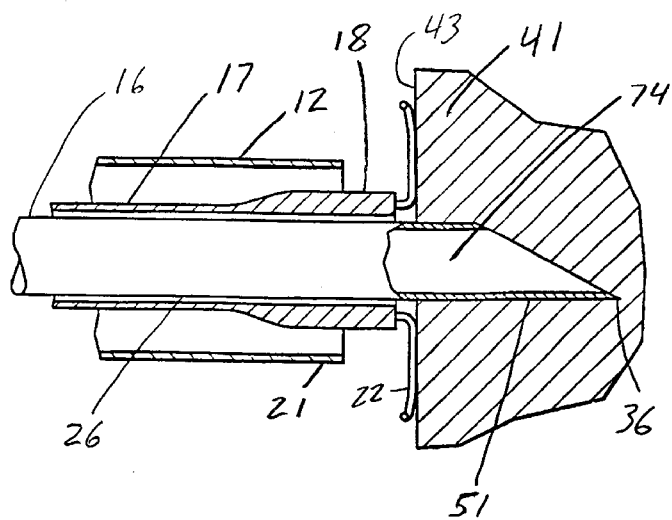
FIG. 11 is an elevational view in partial section of the distal end of the substance delivery member where the sharp distal end of the elongated cannula is extended distally beyond the distal end of the sheath of the substance delivery member.

In the illustrations shown in FIGS. 9–11, the penetration limiters 22 are most preferably Nitinol wire loops as illustrated. However, other materials will be useful for the loop construction, and penetration limiter 22 configurations other than the loops shown will also be useful. The penetration limiters 22 generally will be flexible and fold from a position permitting passage through the second delivery catheter 12 and the like and radially expand when exiting the second delivery catheter where they provide a larger distal area of contact with the tissue 43.

Finally, as seen in FIG. 11, the sharp distal tip 36 of the elongated cannula 16 will extend beyond the distal end 18 of the polymer sheath 17. It will be understood that at this point, the operator will have determined that the device is in the correct position to initiate this movement. Typically and preferably, the polymer sheath 17 will be in contact with a tissue surface 43, as supported and limited by the penetration limiters 22 described above. When in this position, a device like the elongated cannula 16 may then be moved relative to the rest of the device so that it extends below the tissue surface 43 or at least penetrates the tissue surface to permit delivery of a diagnostic or therapeutic substance 25 through its lumen 74.

Regarding the substance delivery member 15, a variety of devices are useful in addition to the illustrated elongated cannula 16. As illustrated, a simple hypodermic tube cut at an oblique angle, as is conventional in the art provides one preferred embodiment. However, it will be realized that other constructions are useful, such as blunt ends, closed ends with radial orifices, bulbous or shaped ends, tapered ends, square cut ends or ends formed into multiple spurs or barbs.

Figure 12:
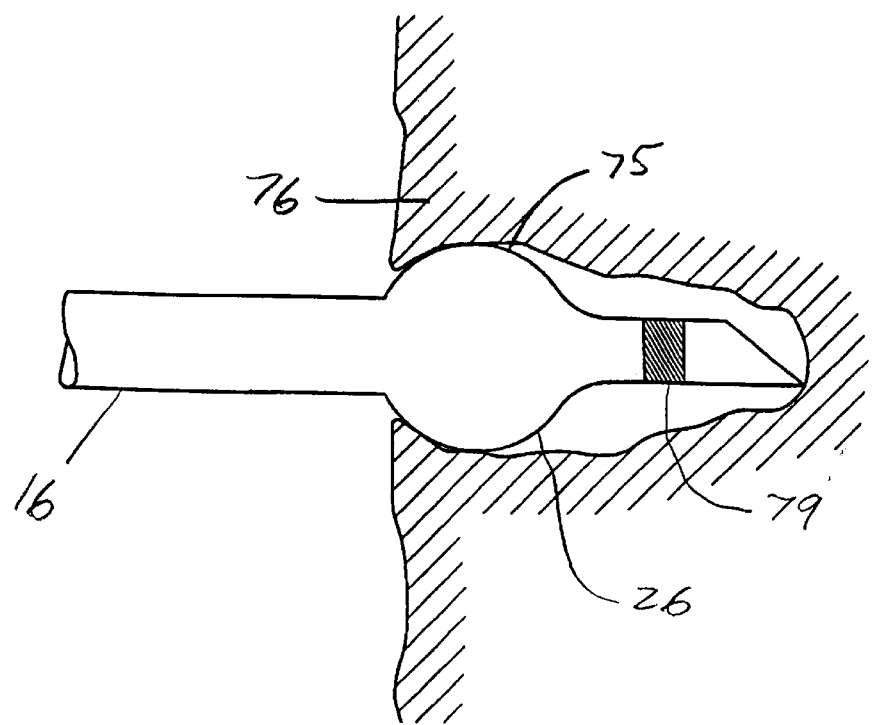
FIG. 12 is an alternative embodiment of the distal end of the elongated cannula of the substance delivery member.

FIG. 12 illustrates the distal end 26 of an elongated cannula 16 having a bulbous portion 75 which can be pushed sub-endocardially during cardiac systole. The heart tissue 76 mechanically captures the bulbous portion 75 to help maintain the position and placement of the distal end 26 of the elongated cannula 16 during substance delivery. Any and all of these constructions are contemplated for use with the present invention, so long as the distal construction chosen is effective to deliver a dose of diagnostic or therapeutic substance 25. The distal end 26 of the elongated cannula may also have a radiopaque marker 79 which is useful for positioning the distal end under flouroscopic visualization.

Referring to FIGS. 1, and 7–9, the motion of the slider 35 is most preferably integral with the motion of the sharp 36 and as such permits a 1:1 relationship between the linear motion of the slider and the distance that the sharp 36 extends. In a preferred embodiment, the slider 35 can be calibrated and provided with detents 77 such that each sub-segment of motion between detents defines a predetermined extension of the sharp 36, e.g., one millimeter. An audible and tactile "click" provided by such arrangement will be useful to the user and assist in the effective and efficient use of the delivery catheter system 10.

In certain embodiments, however, it will be preferable to define the extension of the distal end 26 of the elongated cannula as a fixed distance. In other words, the elongated cannula 16 will move from a retracted position to an extended position, without intermediate adjustments. In an embodiment similar to that shown in FIG. 1, this will result in the slider 35 moving between a first detent 78 and a second detent 81. Alternatively, the slider 35 could be replaced with a lever or a portion of the advancement controller 33 that is squeezed so that the cannula 16 extends upon squeezing and automatically retracts. Finally, in certain embodiments, linear motion of the elongated cannula 16 would be effected with a twisting motion of a screw member which would be mechanically coupled to the elongated cannula 16. In embodiments where adjustable penetration of the distal tip 51 of the elongated cannula 16 is needed the advancement controller 33 can again be provided with detents 77 and calibrated so that each rotation between detents moves the cannula 16 a predetermined distance. Alternatively, in other embodiments, a twist or rotation of the advancement controller 33 between a first position and a second position would move the cannula 16 a predetermined distance, without control or adjustment available to the user.

Figure 13:
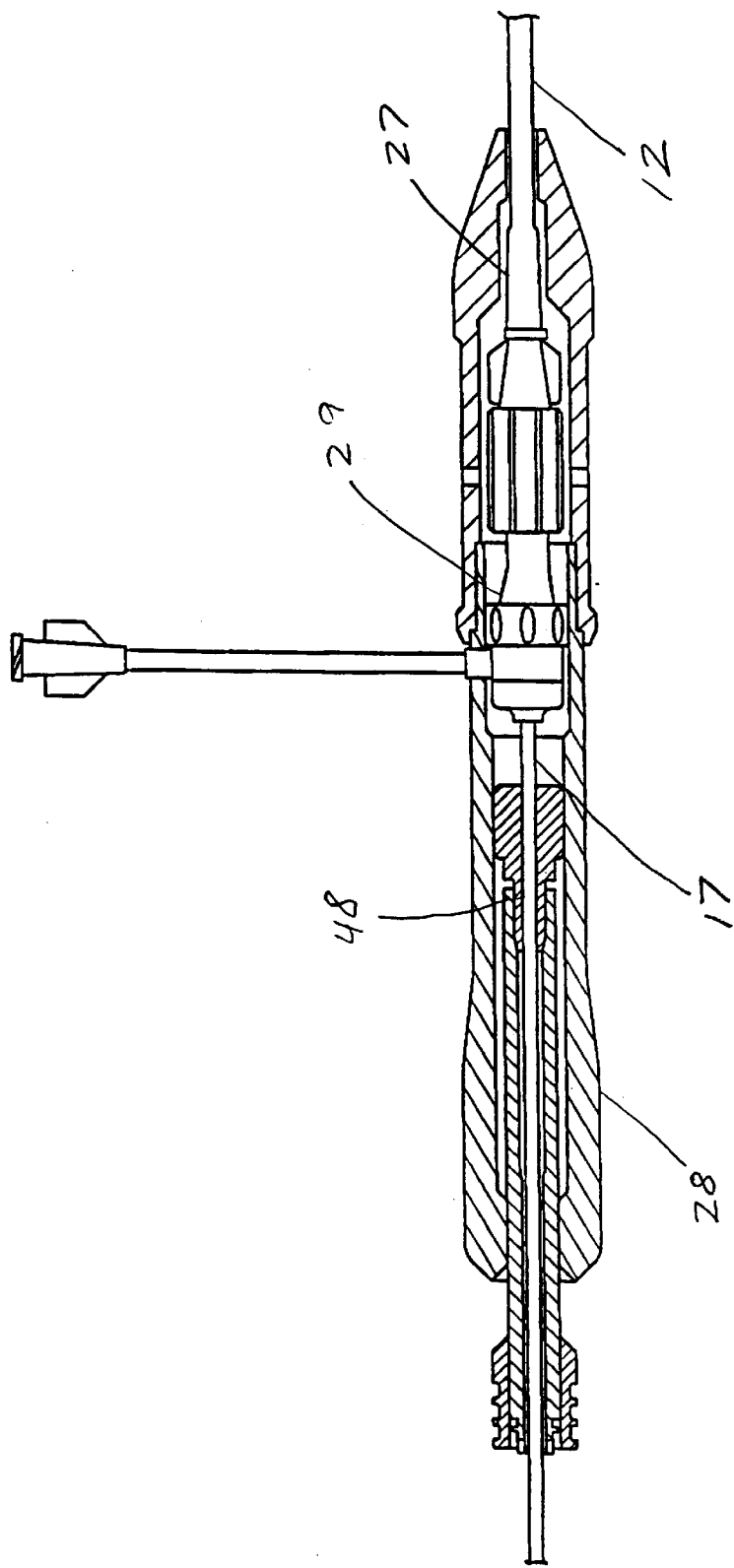
FIG. 13 is an elevational view in partial section of the proximal controller.
Figure 14:
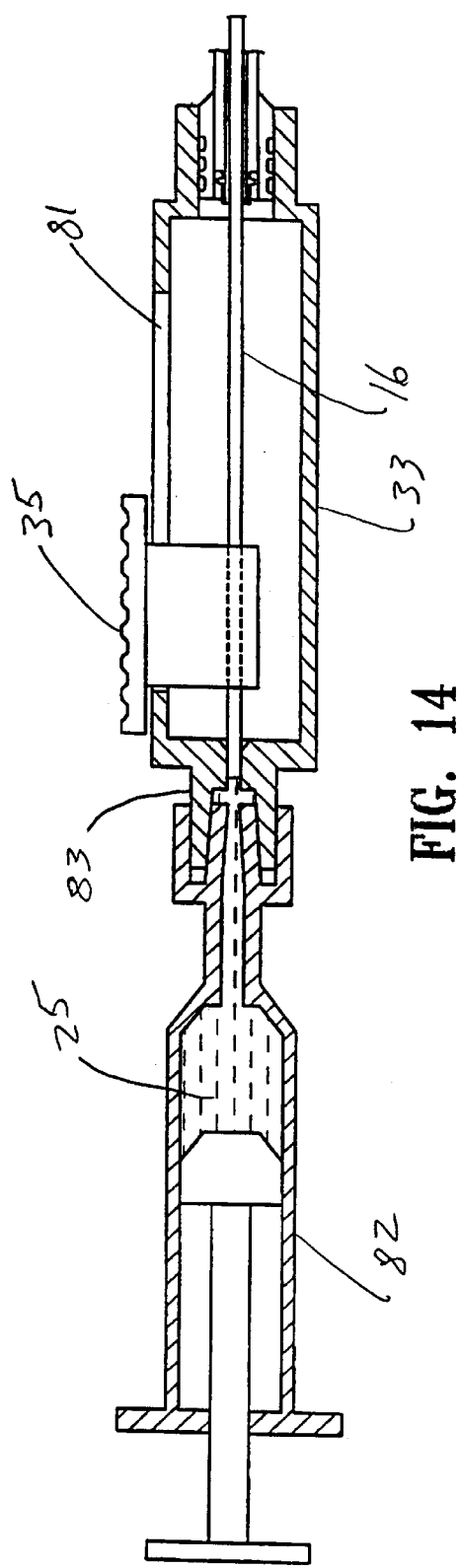
FIG. 14 is an elevational view in partial section of the advancement controller.

Referring to FIG. 13 and FIG. 14, the advancement controller 33 preferably simultaneously provides three functions, namely, polymer sheath 17 advancement, elongated cannula 16 advancement and fluid connection to the distal end 37 of the system 10. The relative motion between the advancement controller 33 and the proximal controller 28 cause the polymer sheath 17 to advance or retract relative to the second delivery catheter 12, as described above. Thus, in use, the first delivery catheter 11 and second delivery catheter 12 are guided and steered to position the distal end 37 of the catheter assembly 10 within a body cavity, and most particularly within the left ventricle 38. Next, the advancement controller 33 is moved relative to the proximal controller 28 and this action extends the polymer sheath 17 toward the tissue surface 43. Upon contact or in proximity of the tissue surface 43, a slider 35 is operated to extend an elongated cannula 16 or other substance delivery device from the distal tip of the polymer sheath 18. The range of motion of the slider 35 is constrained by the length of the slot 81 in which the slider 35 travels. After the elongated cannula 16 has been extended and is lodged in endocardial and/or myocardial tissue 41, a therapeutic or diagnostic substance 25 is injected into the tissue. In the embodiment shown, the substance injection may be effected by a simple hypodermic syringe 82 that is in fluid communication with the proximal end 83 of the advancement controller 33 via any suitable fluid-tight connection, e.g., a standard LuerLok connection. After a dose is administered, the slider 35 is used to retract the elongated cannula 16 and the advancement controller 33 is used to withdraw the polymer sheath 17, if necessary. Further details of the operation of the distal end 37 of the apparatus 10 of the present invention can be observed with reference to the sequence of views set forth in FIGS. 9–11.

Figure 15:
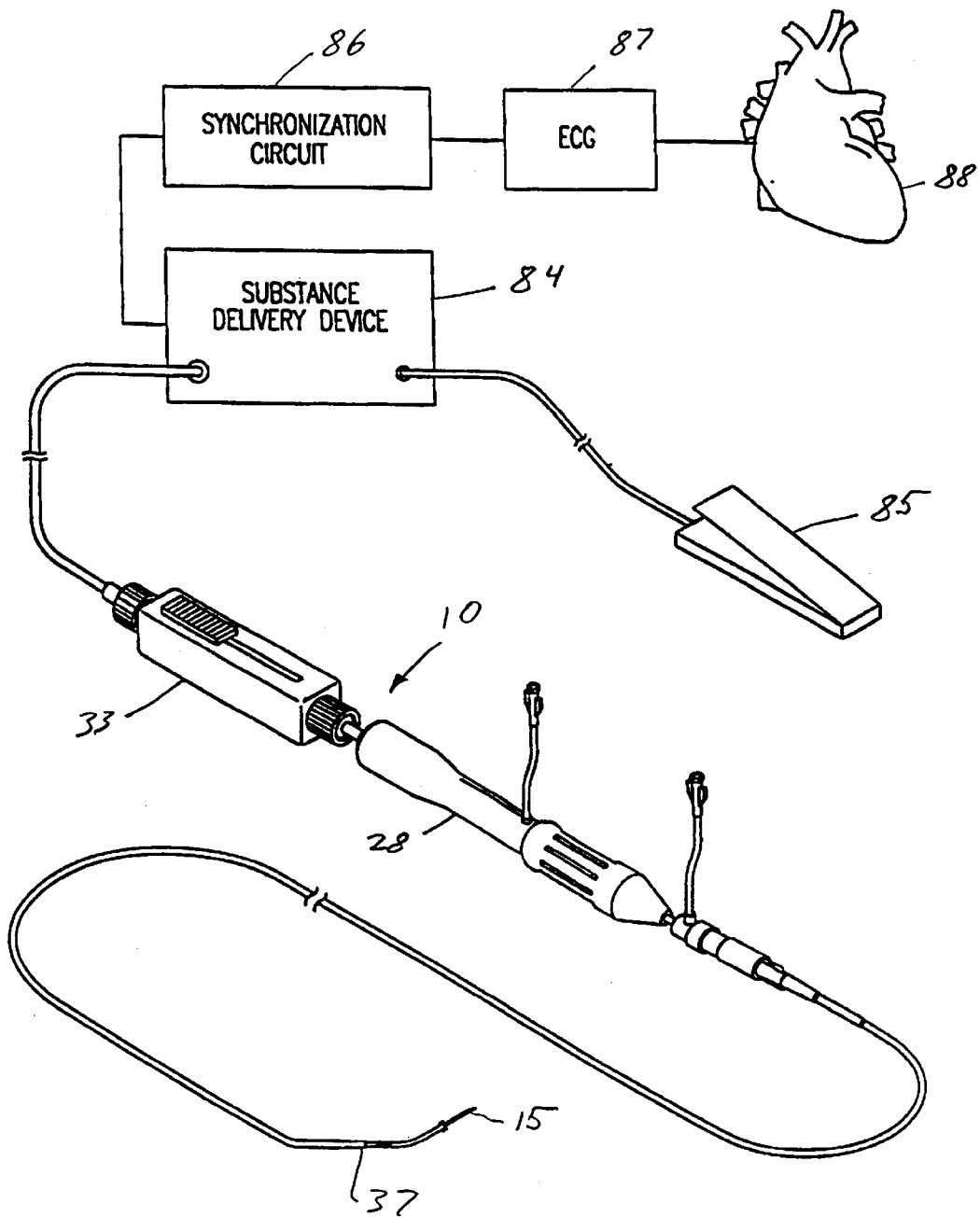
FIG. 15 is a schematic view of an alternative embodiment of the catheter delivery system which incorporates an ECG synchronizer.

Referring now to FIG. 15, an alternate embodiment of the system 10 of the present invention is shown. In this embodiment, the injector is an electronic substance delivery device 84. As shown in the art, electronic substance delivery devices 84 provide a precise, metered amount of a substance upon receiving a command. In a typical application, the signal will preferably be provided by a foot pedal 85. In some embodiments, the depressing of a foot pedal 85 will initiate a dispense cycle and a specific amount of a diagnostic or therapeutic substance 25 will be injected through the substance delivery member 15 and into the tissue. Alternately, the foot pedal 85 can be replaced by a button or trigger switch that forms part of the advancement controller 33 described above or is otherwise attached or affixed to the proximal controller 28 of the catheter. In the embodiment illustrated in FIG. 15, a further refinement is shown, in which the electronic substance delivery device 84 is connected to a synchronization circuit 86, that in turn receives a signal from an ECG 87 or other source of information about the cycle of the heart 88. In some embodiments it may be desirable to time the delivery of the substance 25 to the cardiac cycle 88, and the system 10 shown in FIG. 15 permits such timing to be accomplished. In other embodiments, the substance delivery device 15 is actuated by the extension of the elongated cannula 16, as described above, so that injection occurs upon or immediately after penetration. Alternatively, a signal for an injection, whether manual or automatic, signals a motorized extension mechanism that extends the elongated cannula 16 and follows the extension with an injection, and ultimately with an automated retraction.

Figure 16:
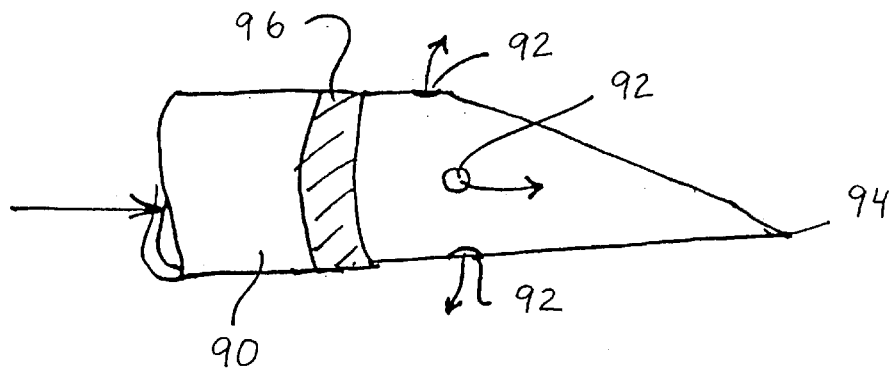
FIG. 16 is a partial side elevation view of the an alternative construction of a distal tip of a device embodying features of the present invention.

As shown in FIG. 16, the distal end 90 can be modified by introducing radial orifices 92. The central lumen may remain open, or may be closed. In the latter case, the radial orifices 92 will provide the only path for flow into the myocardium and will thus tend to force the angiogenic agent over a wide area lateral to the injection site. Additionally, in preferred embodiments, the sharp 94 itself or other structures associated with the distal end 90 preferably possess shape memory and/or are comprised of stainless steel, NITINOL, or other materials known in the art to have such characteristics. Glass and high strength plastic tubing may also be employed. A radiopaque band 96 may be provided as with the previously discussed embodiments.

Figure 17:
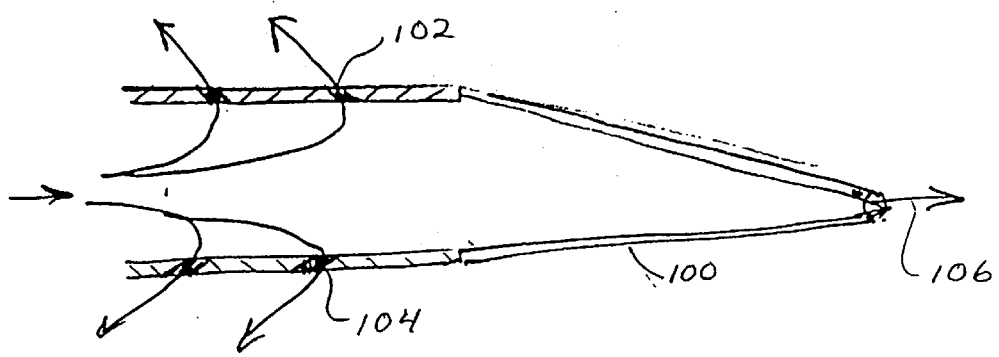
FIG. 17 is a partial side elevation view of the an alternative construction of a distal tip of a device embodying features of the present invention.

The movement of the angiogenic agent or other fluid can additionally be useful to help ensure retention of the sharp and aid in dissection and diffusion. As shown in FIG. 17, in certain embodiments, the distal end 100 has angled orifices 102 and 104 which are selectively arrayed within the distal end construction so that the directionality of the substance flow is altered as shown by the arrows. The resultant force will tend to retain the distal end 100 in place, rather than dislodge it, or in some cases will actually drive the distal end deeper into the tissue. AS shown, it may be necessary to provide an orifice 106 at the tip in order to regulate the effect of the rear facing orifices 102 and 104.

Figure 18:
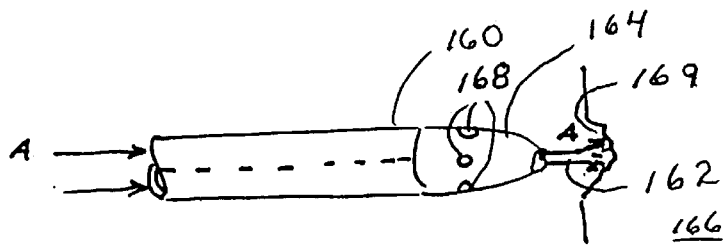
FIG. 18 is a partial side elevation view of the distal tip of a device embodying features of the present invention shown penetrating the myocardium.
Figure 19:
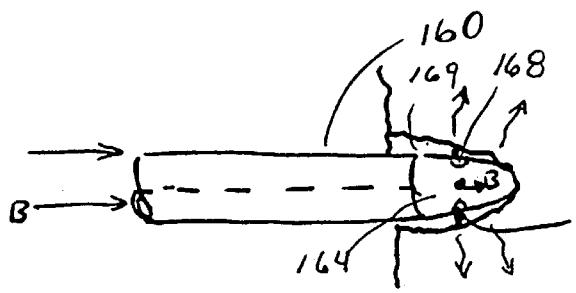
FIG. 19 depicts the apparatus of FIG. 18 after deeper penetration into the myocardium.

FIGS. 18 and 19 illustrate another embodiment of the present invention having a catheter or probe 160 in which high pressure fluid is emitted from the distal end 164 to dissect tissue. The catheter 160 may be a single lumen or multi-lumen catheter. In the embodiments shown in FIGS. 18 and 19, the angiogenic substance or another of the fluids that comprise part of the administered dose is forced out at sufficient velocity and pressure such that an area of disturbance or dissection is created in the myocardium that is larger than the channel formed by the dissection of a penetrating distal tip alone.

In one embodiment, the substance may be a chemical that ablates tissue, a chemical denervation agent or a combination of the two with a fluid to aid delivery. Thus, as seen in FIG. 18, catheter 160 emits a jet of fluid 162 from the distal end 164 which impinges on a tissue section 166 disrupting the tissue. As seen in FIG. 19, a combination of this tissue disruption and mechanical dissection result in the penetration of the distal end 164 into the tissue. If a dual lumen delivery device is employed, the fluid stream 162 that creates the dissection may be selectively stopped and an angiogenic agent can be emitted from orifices 168 which are in fluid communication with another lumen (not shown) within the catheter 160 as shown by the arrows. This embodiment will be particularly useful when it is determined that the sharp needs to be eliminated from the distal tip. The high velocity fluid stream 162 impinges on the tissue 166, creating a channel 169 formerly created solely by dissecting distal end 164.

During the process fluid stream 162 alternately or optionally provides deposition of an angiogenic agent or dissection fluid alone that serves as a precursor to deposition. Additionally, in other embodiments similar to that shown in FIGS. 18 and 19 where radial orifices are provided in the distal end lateral fluid flow, e.g. liquids or gases like $CO_2$ can be forced through the orifices and multiple jets will create dissection planes and other collateral damage. Additionally, by selective administration of the appropriate fluid, tissue can be either ablated or denerved. Such embodiments and administration methods will be employed to create sites more receptive to many of the angiogenic agents contemplated for use with the present invention. Preferably, several lateral orifices will permit the angiogenic agent to be simultaneously delivered at several depths within the myocardium. Finally, as explained in detail above with reference to FIG. 17, if the lateral orifices are disposed at angles such that their discharge axes are inclined toward the tissue surface the backwards-firing "jets" will help to push the device into the tissue or at least assist to secure it within the surrounding tissue when the device is inserted into the myocardium.

Another alternate technique to ensure stable placement of the distal end of the delivery device is to heat a portion of the distal end of the device. This heating may be to a temperature sufficient to ablate tissue, but may be much lower so long as the "hot tip" causes the distal end to "stick" to the tissue in order to maintain placement during substance delivery. Any of a number of heat transfer techniques can be used, either by transmission of energy through the catheter or intraoperative probe or via absorption of energy emanating from an extracorporeal source.

Figure 20:
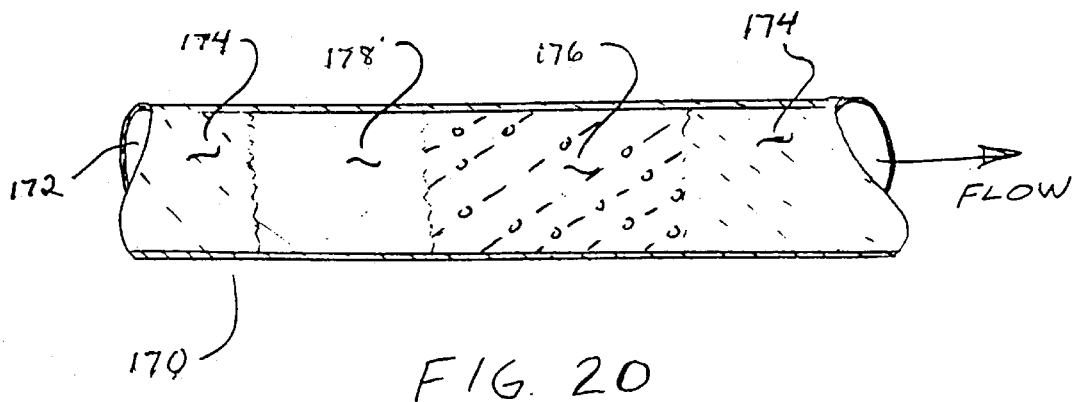
FIG. 20 is a partial cross-sectional elevation view of a conduit carrying an angiogenic agent and other substances useful in conjunction with the present invention.

Another aspect of the present innovation is the visualization of the angiogenic agents both while in the reservoir, in situ during administration and in vivo after administration. In order to effect visualization of the bolus of delivered substance, it is contemplated that, as explained above, in preferred embodiments, the angiogenic agent or a diagnostic material or other substance be radiopaque. Referring to FIG. 20, a catheter 170 has a conduit 172 which is filled with one or more substances, preferably separated by marker substances. In the example illustrated, a carrier fluid 174 fills a section of the device. A radiopaque marker substance 176 precedes a dose of the angiogenic agent 178, which in turn is followed by carrier fluid 174, thereby separating doses. The portion of the conduit 172 distal of the angiogenic agent 178 is preferably filled with the radiopaque marker substance 176 to provide imaging/navigation. However, alternatively the radiopaque marker substance 176 can be the angiogenic substance itself, in which case the clear demarcation seen in FIG. 20 will not be present. Alternatively, as shown in FIG. 20, a length of a separate radiopaque or other marker substance 176 that can be expressed prior to delivery of the angiogenic agent to the tissue may be provided.

In any of the embodiments of FIG. 20, the radiopaque fluid or other marker substance, allows the physician to visualize delivery of the appropriate volume of drug by visualizing the advance of the radiopaque separators. When the angiogenic agent is delivered, the radiopaque fluid will be flushed from tube, and thus it will be known that a full dose has reached the tip of the delivery tube and there will be no waste or excess administration. In certain embodiments, where the angiogenic agent is a semi-solid "pellet" instead of a liquid, the pellet itself is preferably radiopaque. In any of these embodiments, another function served by the administration of a radiopaque marker with the angiogenic agent will be to mark the regions of deposition so that a surrounding area of the tissue region may be properly treated with other doses. Alternatively, or in conjunction with an administered substance, the device itself can be made visible by the inclusion of radiopaque markers, which is well known by those skilled in the art.

As disclosed in U.S. Pat. No. 5,840,049 it is advantageous to place an angiogenic agent into the sites where energy has been introduced to cause revascularization in a TMR procedure. It is believed, based upon preliminary data, that delivery of an angiogenic agent to a TMR site results in the most potent neovasculogenesis. TMR causes tissue damage in a region surrounding the site where energy has been introduced. Various energy sources have been used for TMR including laser energy, RF energy and ultrasonic energy. It is believed that the tissue damage provides benefits by denervating tissue and that it also stimulates new blood vessel growth. The new blood vessel growth stimulated by TMR is apparently enhanced or supplemented by the introduction of an angiogenic agent to the TMR site.

Conversely, the administration of growth factors alone may not be optimal. Thus, in one preferred embodiment an optical fiber or RF electrode is delivered down a central lumen of a first delivery catheter and then withdrawn and replaced by a delivery tube, which is then used to administer an angiogenic agent according to any of the techniques set forth above. Alternatively, the physician can leave the first delivery catheter in place and deliver an angiogenic agent through the lumen of the first delivery catheter to the TMR site. Alternatively, multiple lumen embodiments permit energy and angiogenic agents to be delivered sequentially, along with marker substances and other fluids as previously described.

In terms of the adjunctive (with TMR) embodiments of the present invention, the introduction of energy to a tissue site includes all forms of TMR, whether the "channel" traditionally described is formed or not. Additionally, the adjunctive use described herein includes the application of energy to merely disturb or disrupt the tissue. The enhancement of neovasculogenesis may occur due to subtle tissue effects. Such tissue effects may be stimulated by limited energy introduction, such that, in contrast to traditional TMR, no "channel" is formed. Such limited energy deposition may only serve to disturb or disrupt tissue locally while enhancing the uptake of angiogenic agents. For example, a device with a heated distal tip would be used in place of either a sharp or a TMR channel forming device in certain embodiments, e.g., the distal construction shown in FIGS. 18 and 19. This use may be preferable in cases where a simple injection or penetration does not create the disruption of the other techniques discussed above. In other embodiments, the addition of non-thermal energy, particularly ultrasound or acousto-optic affects can be used to drive the angiogenic agent into the surrounding tissue or activate or alter the characteristics of the substance, including in certain embodiments, using adjunctive energy to fracture microspheres containing angiogenic agent.

The present invention also encompasses methods of administering an angiogenic agent. In methods performed in accordance with the present invention, a delivery device is placed in contact with a heart wall and a dose of an angiogenic agent is introduced into the heart tissue. The administration may be timed to the heart cycle, and the step of placing the delivery device in contact with the heart wall can be preceded by piercing the wall. In certain adjunctive embodiments, the step of administering the angiogenic agent is performed after a the delivery of energy has disturbed the tissue, or in some cases the step of administering the angiogenic agent follows the step of performing TMR.

While particular forms of the invention have been illustrated and described, it will be apparent that various modifications can be made without departing from the spirit and scope of the invention. Accordingly, it is not intended that the invention be limited, except as by the appended claims.

What is claimed is:

1. Apparatus for delivering a dose of an angiogenic substance to a desired region of a patient's heart comprising:
   an elongated shaft having a proximal end;
   a distal end configured to penetrate the desired region of the patient's heart, wherein the distal end has a radiopaque marker;
   a handpiece proximal to the distal end;
   a reservoir containing the angiogenic substance;
   an inner lumen extending within the elongated shaft to the distal end which is in fluid communication with the reservoir of the angiogenic substance;
   an orifice in the tip of the distal end in fluid communication with the inner lumen for delivering a first portion of the angiogenic substance into the desired region of the patient's heart; and
   at least one angled radial orifice in the distal end in fluid communication with the inner lumen, wherein a second portion of the angiogenic substance is delivered over a wide lateral area of the desired region of the patient's heart, the movement of the second portion of the angiogenic substance through the at least one angled radial orifice in a rear facing direction from the orifice helps ensure retention of the distal end in the desired region of the patient's heart, and further wherein the movement of the first portion of the angiogenic substance through the orifice regulates the effect of the movement of the second portion of the angiogenic substance through the at least one angled radial orifice.

2. The apparatus of claim 1 wherein the elongated shaft is a catheter.

3. The apparatus of claim 1 wherein the elongated shaft is an intraoperative probe.

4. The apparatus of claim 1, further comprising a metered dispensing system.

5. The apparatus of claim 1 wherein the distal end of the shaft further comprises at least one sharp.

6. The apparatus of claim 1 wherein the elongate shaft has at least one additional lumen.

7. The apparatus of claim 6 wherein at least one of the plurality of lumens is in fluid communication with a source of a fluid other than the angiogenic substance.

8. The apparatus of claim 1 further comprising a distal tissue contact device for tissue injury which includes a conduit connected to a source of fluid which can be delivered at a pressure and velocity sufficient to disrupt tissue.

9. An apparatus for injection of at least one dose of an angiogenic agent to a desired region of a patient's heart which is synchronized to a cardiac cycle of the patient's heart, comprising:

an injection device;

an elongated shaft having a proximal end connected to the injection device and at least one lumen extending within the elongated shaft in fluid communication with the injection device;

a solenoid connected to the injection device to control the dosage amount of the angiogenic agent dispensed by the injection device when the solenoid is pulsed by a signal related to the cardiac cycle of the patient's heart, wherein the at least one lumen contains in addition to the angiogenic agent a fluid and a marker substance;

an orifice in a tip of a distal end of the injection device for delivering a first portion of the angiogenic agent into the desired region of the patient's heart; and at least one angled radial orifice in the distal end of the injection device, wherein a second portion of the angiogenic agent is delivered over a wide lateral area of the desired region of the patient's heart, the movement of the second portion of the angiogenic agent through the at least one angled radial orifice in a rear facing direction from the orifice helps ensure retention of the distal end in the desired region of the patient's heart, and further wherein the movement of the first portion of the angiogenic agent through the orifice regulates the effect of the movement of the second portion of the angiogenic agent through the at least one angled radial orifice.

* * * * *